(12) United States Patent
Gualano

(10) Patent No.: US 9,554,875 B2
(45) Date of Patent: *Jan. 31, 2017

(54) METHOD FOR PRODUCING A CUSTOMIZED ORTHODONTIC APPLIANCE

(71) Applicant: RMO, Inc., Denver, CO (US)

(72) Inventor: Christophe Gualano, Colomiers (FR)

(73) Assignee: RMO, Inc., Denver, CO (US)

( * ) Notice: Subject to any disclaimer, the term of this patent is extended or adjusted under 35 U.S.C. 154(b) by 14 days.

This patent is subject to a terminal disclaimer.

(21) Appl. No.: 14/743,142

(22) Filed: Jun. 18, 2015

(65) Prior Publication Data

US 2015/0282897 A1 Oct. 8, 2015

Related U.S. Application Data

(63) Continuation of application No. 13/762,455, filed on Feb. 8, 2013, now abandoned, which is a
(Continued)

(51) Int. Cl.
*A61C 3/00* (2006.01)
*A61C 7/00* (2006.01)
(Continued)

(52) U.S. Cl.
CPC .............. *A61C 7/002* (2013.01); *A61C 7/143* (2013.01); *A61C 7/16* (2013.01); *A61C 7/28* (2013.01);
(Continued)

(58) Field of Classification Search
CPC ......... A61C 7/002; A61C 7/141; A61C 7/143; A61C 7/145; A61C 7/16; A61C 7/28; A61C 7/285
See application file for complete search history.

(56) References Cited

U.S. PATENT DOCUMENTS 626,476 A 6/1899 Angle
1,890,487 A 12/1932 Angle
(Continued)

FOREIGN PATENT DOCUMENTS

DE 8903611 8/1990
DE 69228472 10/1999
(Continued)

OTHER PUBLICATIONS

U.S. Appl. No. 10/821,699, filed Apr. 9, 2004, Ricketts.
(Continued)

*Primary Examiner* — George Manuel
(74) *Attorney, Agent, or Firm* — Sheridan Ross P.C.

(57) ABSTRACT

The present disclosure is directed, at least in part, to a self ligating orthodontic bracket system that includes a rotatable member for securing an archwire within a slot of a bracket. Embodiments of the orthodontic bracket system disclosed herein include a bracket body containing the archwire slot as well as tie wings for attaching various orthodontic devices (e.g., elastomeric bands) to the bracket. The rotatable member is rotatable in a first direction (e.g., counter clockwise) relative to a body of the bracket for securing or locking the archwire within the slot, and for rotating in an opposite direction (e.g., a clockwise direction) relative to the bracket body for unsecuring or unlocking the archwire so that it is substantially unrestrained from exiting the slot. Other embodiments include an orthodontic appliance and method of producing and using the same, and preferably employed in a lingual orthodontic system, that includes friction reducing features between an interior of an archwire slot portion of the appliance and an archwire placed within the archwire slot.

19 Claims, 17 Drawing Sheets

Related U.S. Application Data continuation-in-part of application No. 13/117,085, filed on May 26, 2011, now Pat. No. 8,376,739, application No. 14/743,142, which is a continuation of application No. 13/762,455, filed on Feb. 8, 2013, now abandoned, which is a continuation-in-part of application No. 12/937,588, filed on Dec. 15, 2010, now Pat. No. 8,371,847, application No. 14/743,142, which is a continuation of application No. 13/762,455, filed on Feb. 8, 2013, now abandoned, which is a continuation-in-part of application No. 13/595,548, filed on Aug. 27, 2012, now Pat. No. 8,585,399, which is a continuation of application No. 11/852,057, filed on Sep. 7, 2007, now Pat. No. 8,251,697, application No. 14/743,142, which is a continuation of application No. 13/762,455, filed on Feb. 8, 2013, now abandoned, which is a continuation-in-part of application No. 12/724,159, filed on Mar. 15, 2010, now Pat. No. 8,485,816.

(60) Provisional application No. 61/518,927, filed on May 12, 2011, provisional application No. 60/824,891, filed on Sep. 7, 2006, provisional application No. 61/160,653, filed on Mar. 16, 2009.

(51) Int. Cl.
*A61C 7/16* (2006.01)
*A61C 7/28* (2006.01)
*A61C 7/14* (2006.01)

(52) U.S. Cl.
CPC ............... *A61C 7/285* (2013.01); *A61C 7/141* (2013.01); *A61C 7/145* (2013.01)

(56) References Cited

U.S. PATENT DOCUMENTS

| | | |
|---|---|---|
| 2,011,575 A | 8/1935 | Ford |
| 2,104,192 A | 1/1938 | Ford |
| 2,196,515 A | 4/1940 | Atkinson |
| 3,028,671 A | 4/1962 | Berger |
| 3,055,110 A | 9/1962 | Kesling |
| 3,158,934 A | 12/1964 | Waldman |
| 3,193,930 A | 7/1965 | Bien |
| 3,391,461 A | 7/1968 | Johnson |
| 3,435,527 A | 4/1969 | Kesling |
| 3,494,034 A | 2/1970 | Kesling |
| 3,504,438 A | 4/1970 | Wittman et al. |
| 3,526,961 A | 9/1970 | Kesling |
| 3,765,091 A | 10/1973 | Northcutt |
| 3,798,773 A | 3/1974 | Northcutt |
| 3,838,514 A | 10/1974 | Polak |
| 3,854,207 A | 12/1974 | Wildman |
| 3,874,080 A | 4/1975 | Wallshein |
| 3,916,526 A | 11/1975 | Schudy |
| 3,964,156 A | 6/1976 | Williams et al. |
| 3,975,824 A | 8/1976 | Lee |
| 3,985,282 A | 10/1976 | Miller et al. |
| 3,987,547 A | 10/1976 | Moss |
| 4,015,334 A | 4/1977 | Moss |
| 4,028,809 A | 6/1977 | Wallshein |
| 4,083,113 A | 4/1978 | Miller et al. |
| 4,103,423 A | 8/1978 | Kessel |
| 4,134,208 A | 1/1979 | Pearlman |
| 4,171,568 A | 10/1979 | Forster |
| 4,172,999 A | 10/1979 | Leidich |
| 4,183,141 A | 1/1980 | Dellinger et al. |
| 4,192,070 A | 3/1980 | Lemchen et al. |
| 4,193,195 A | 3/1980 | Merkel et al. |
| 4,197,642 A | 4/1980 | Wallshein |
| 4,212,638 A | 7/1980 | Korn |
| 4,219,617 A | 8/1980 | Wallshein |
| D256,950 S | 9/1980 | Sable |
| 4,242,085 A | 12/1980 | Wallshein |
| 4,248,587 A | 2/1981 | Kurz |
| 4,260,375 A | 4/1981 | Wallshein |
| 4,284,405 A | 8/1981 | Dellinger |
| 4,299,569 A | 11/1981 | Frantz |
| 4,322,206 A | 3/1982 | Reynolds |
| 4,350,487 A | 9/1982 | Kesling et al. |
| 4,354,834 A | 10/1982 | Wilson |
| 4,386,908 A | 6/1983 | Kurz |
| 4,415,330 A | 11/1983 | Daisley et al. |
| 4,419,078 A | 12/1983 | Pletcher |
| 4,430,061 A | 2/1984 | Webb et al. |
| 4,455,137 A | 6/1984 | Diamond |
| 4,462,800 A | 7/1984 | Jones |
| 4,478,577 A | 10/1984 | Warren, Jr. |
| 4,498,867 A | 2/1985 | Kesling |
| 4,511,331 A | 4/1985 | Scebold et al. |
| 4,527,975 A | 7/1985 | Ghafari et al. |
| 4,529,382 A | 7/1985 | Creekmore |
| 4,531,991 A | 7/1985 | Ziemek et al. |
| 4,545,760 A | 10/1985 | Forster |
| 4,551,095 A | 11/1985 | Mason |
| 4,575,337 A | 3/1986 | Fujita |
| 4,626,209 A | 12/1986 | Tsai et al. |
| 4,639,218 A | 1/1987 | Jones et al. |
| 4,659,309 A | 4/1987 | Merkel |
| 4,661,059 A | 4/1987 | Kanno |
| D290,040 S | 5/1987 | Kelly |
| 4,669,979 A | 6/1987 | Snead |
| 4,669,981 A | 6/1987 | Kurz |
| D291,919 S | 9/1987 | Reynolds |
| 4,700,697 A | 10/1987 | Mundell et al. |
| 4,712,999 A | 12/1987 | Rosenberg |
| 4,752,221 A | 6/1988 | Hanson et al. |
| 4,773,853 A | 9/1988 | Kussick |
| 4,781,334 A | 11/1988 | Derichs |
| 4,781,582 A | 11/1988 | Kesling |
| 4,793,804 A | 12/1988 | Schudy |
| 4,795,342 A | 1/1989 | Jones |
| 4,799,882 A | 1/1989 | Kesling |
| 4,819,316 A | 4/1989 | Rossini et al. |
| 4,820,151 A | 4/1989 | Pospisil |
| 4,838,786 A | 6/1989 | Reher et al. |
| 4,854,866 A | 8/1989 | Wilson |
| 4,859,179 A | 8/1989 | Kesling |
| 4,900,251 A | 2/1990 | Andreasen |
| 4,917,602 A | 4/1990 | Broussard |
| 4,927,360 A | 5/1990 | Pospisil |
| 4,927,362 A | 5/1990 | Snead |
| 4,954,080 A | 9/1990 | Kelly et al. |
| 4,963,092 A | 10/1990 | Snead |
| 4,975,052 A | 12/1990 | Spencer et al. |
| 4,997,182 A | 3/1991 | Kussick |
| 5,022,854 A | 6/1991 | Broughton et al. |
| 5,030,089 A | 7/1991 | Kawaguchi |
| 5,035,614 A | 7/1991 | Greenfield |
| 5,044,945 A | 9/1991 | Peterson |
| 5,057,012 A | 10/1991 | Kesling |
| 5,059,119 A | 10/1991 | Snead |
| 5,062,794 A | 11/1991 | Miura |
| 5,066,225 A | 11/1991 | Forbes Jones et al. |
| D322,482 S | 12/1991 | Ianieri et al. |
| 5,095,602 A | 3/1992 | Reher et al. |
| 5,120,218 A | 6/1992 | Hanson |
| 5,125,831 A | 6/1992 | Pospisil |
| 5,125,832 A | 6/1992 | Kesling |
| 5,127,828 A | 7/1992 | Suyama |
| 5,133,740 A | 7/1992 | Kussick |
| 5,151,028 A | 9/1992 | Snead |
| 5,154,607 A | 10/1992 | Hanson |
| 5,158,452 A | 10/1992 | Franseen et al. |
| 5,160,261 A | 11/1992 | Peterson |
| 5,161,969 A | 11/1992 | Pospisil et al. |
| D331,975 S | 12/1992 | Pospisil |
| 5,183,388 A | 2/1993 | Kumar |
| 5,203,804 A | 4/1993 | Nikutowski et al. |
| 5,224,858 A | 7/1993 | Hanson |
| 5,226,814 A | 7/1993 | Allen |

(56) References Cited

U.S. PATENT DOCUMENTS

| | | |
|---|---|---|
| 5,230,620 A | 7/1993 | Watanabe |
| 5,238,402 A | 8/1993 | Rohlcke et al. |
| 5,242,299 A | 9/1993 | Yoshida |
| D340,523 S | 10/1993 | Barngrover |
| 5,252,066 A | 10/1993 | Fairhurst |
| 5,254,002 A | 10/1993 | Reher et al. |
| 5,267,855 A | 12/1993 | Tuneberg |
| 5,269,680 A | 12/1993 | Kawaguchi |
| 5,277,581 A | 1/1994 | Peterson |
| 5,288,229 A | 2/1994 | Huff et al. |
| 5,292,248 A | 3/1994 | Schultz |
| 5,299,934 A | 4/1994 | Suyama |
| 5,302,117 A | 4/1994 | Kraut et al. |
| 5,302,121 A | 4/1994 | Gagin |
| 5,320,525 A | 6/1994 | Forster |
| 5,320,526 A | 6/1994 | Tuneberg |
| 5,322,435 A | 6/1994 | Pletcher |
| 5,322,613 A | 6/1994 | Ohira |
| 5,356,288 A | 10/1994 | Cohen |
| 5,358,402 A | 10/1994 | Reed et al. |
| 5,362,232 A | 11/1994 | Franseen et al. |
| 5,362,233 A | 11/1994 | Thompson |
| 5,380,196 A | 1/1995 | Kelly et al. |
| 5,383,784 A | 1/1995 | Sernetz |
| 5,395,238 A | 3/1995 | Andreiko et al. |
| D358,649 S | 5/1995 | Moschik |
| D358,650 S | 5/1995 | Moschik |
| D359,776 S | 6/1995 | Hilgers |
| 5,439,379 A | 8/1995 | Hansen |
| 5,441,408 A | 8/1995 | Moschik |
| 5,441,409 A | 8/1995 | Tuneberg |
| 5,443,384 A | 8/1995 | Franseen et al. |
| 5,454,716 A | 10/1995 | Banerjee et al. |
| 5,464,349 A | 11/1995 | Andreiko et al. |
| 5,470,228 A | 11/1995 | Franseen et al. |
| 5,474,444 A | 12/1995 | Wildman |
| 5,474,445 A | 12/1995 | Voudouris |
| 5,505,616 A | 4/1996 | Harwell |
| 5,522,725 A | 6/1996 | Jordan et al. |
| 5,545,037 A | 8/1996 | Takeshi |
| 5,556,277 A | 9/1996 | Yawata et al. |
| 5,562,445 A | 10/1996 | DeVincenzo et al. |
| 5,588,833 A | 12/1996 | Risse |
| 5,595,484 A | 1/1997 | Orikasa et al. |
| 5,597,302 A | 1/1997 | Pospisil et al. |
| 5,607,301 A | 3/1997 | Roman |
| 5,616,026 A | 4/1997 | Cash |
| 5,618,175 A | 4/1997 | Reher et al. |
| 5,620,321 A | 4/1997 | Thornburg et al. |
| 5,622,494 A | 4/1997 | Andreiko et al. |
| 5,653,588 A | 8/1997 | Moschik |
| 5,685,711 A | 11/1997 | Hanson |
| 5,692,898 A | 12/1997 | Orikasa et al. |
| 5,707,231 A | 1/1998 | Watt et al. |
| 5,720,611 A | 2/1998 | Teng |
| 5,727,941 A | 3/1998 | Kesling |
| 5,729,768 A | 3/1998 | Fields et al. |
| 5,738,514 A | 4/1998 | DeVincenzo et al. |
| 5,746,592 A | 5/1998 | Nezu et al. |
| 5,746,594 A | 5/1998 | Jordan et al. |
| RE35,863 E | 7/1998 | Sachdeva et al. |
| 5,779,470 A | 7/1998 | Kussick |
| 5,791,897 A | 8/1998 | Wildman |
| 5,810,583 A | 9/1998 | Doyle |
| 5,820,371 A | 10/1998 | Forster |
| 5,829,972 A | 11/1998 | Farzin-Nia |
| 5,829,975 A | 11/1998 | Gold |
| 5,857,849 A | 1/1999 | Kurz |
| 5,871,350 A | 2/1999 | Clark et al. |
| 5,879,157 A | 3/1999 | Scheu |
| 5,885,073 A | 3/1999 | Kussick |
| 5,885,074 A | 3/1999 | Hanson |
| 5,890,891 A | 4/1999 | Doyle |
| 5,908,293 A | 6/1999 | Voudouris |
| 5,915,550 A | 6/1999 | Gartz |
| 6,036,489 A | 3/2000 | Brosius |
| 6,053,458 A | 4/2000 | Meyer |
| 6,053,729 A | 4/2000 | Brehm et al. |
| 6,053,759 A | 4/2000 | Kunert et al. |
| 6,071,119 A | 6/2000 | Christoff et al. |
| 6,086,364 A | 7/2000 | Brunson |
| 6,109,916 A | 8/2000 | Wilcko et al. |
| 6,123,544 A | 9/2000 | Cleary |
| 6,126,441 A | 10/2000 | Tenti |
| 6,142,775 A | 11/2000 | Hansen et al. |
| 6,162,051 A | 12/2000 | Brehm et al. |
| 6,190,165 B1 | 2/2001 | Andreiko et al. |
| 6,193,508 B1 | 2/2001 | Georgakis |
| 6,206,690 B1 | 3/2001 | Vargas |
| 6,217,322 B1 | 4/2001 | Kesling |
| 6,220,857 B1 | 4/2001 | Abels |
| 6,227,849 B1 | 5/2001 | Brehm et al. |
| 6,234,792 B1 | 5/2001 | DeVincenzo |
| 6,264,469 B1 | 7/2001 | Moschik |
| 6,276,930 B1 | 8/2001 | Pozzi |
| 6,280,185 B1 | 8/2001 | Palmer et al. |
| 6,302,688 B1 | 10/2001 | Jordan et al. |
| 6,347,939 B2 | 2/2002 | Abels |
| 6,354,834 B2 | 3/2002 | Kanomi |
| 6,358,043 B1 | 3/2002 | Mottate et al. |
| 6,358,046 B1 | 3/2002 | Brehm et al. |
| 6,361,314 B1 | 3/2002 | Garton, Jr. |
| 6,361,317 B1 | 3/2002 | Rahman |
| 6,368,105 B1 | 4/2002 | Voudouris et al. |
| 6,371,760 B1 | 4/2002 | Zavilenski et al. |
| 6,394,798 B1 | 5/2002 | Huff et al. |
| 6,428,314 B1 | 8/2002 | Jones, Jr. et al. |
| 6,461,157 B1 | 10/2002 | Kussick |
| 6,478,579 B1 | 11/2002 | Brusse |
| 6,491,519 B1 | 12/2002 | Clark et al. |
| 6,506,049 B2 | 1/2003 | Hanson |
| 6,582,226 B2 | 6/2003 | Jordan et al. |
| 6,592,366 B2 | 7/2003 | Triaca et al. |
| 6,607,383 B2 | 8/2003 | Abels et al. |
| 6,616,445 B2 | 9/2003 | Abels et al. |
| 6,655,957 B2 | 12/2003 | Abels et al. |
| 6,655,958 B2 | 12/2003 | Abels et al. |
| 6,656,767 B1 | 12/2003 | King et al. |
| 6,659,766 B2 | 12/2003 | Abels et al. |
| 6,659,767 B2 | 12/2003 | Abels et al. |
| 6,663,385 B2 | 12/2003 | Tepper |
| 6,668,834 B1 | 12/2003 | Zikria |
| 6,695,612 B2 | 2/2004 | Abels et al. |
| 6,705,862 B2 | 3/2004 | Schultz |
| 6,709,268 B2 | 3/2004 | Pospisil et al. |
| 6,733,286 B2 | 5/2004 | Abels et al. |
| 6,769,910 B1 | 8/2004 | Pantino |
| 6,776,613 B2 | 8/2004 | Orikasa |
| 6,776,614 B2 | 8/2004 | Wiechmann et al. |
| 6,846,178 B2 | 1/2005 | Freeman, Jr. et al. |
| 6,863,528 B2 | 3/2005 | Lin |
| 6,877,982 B2 | 4/2005 | Williams |
| 6,893,257 B2 | 5/2005 | Kelly |
| 6,903,262 B2 | 6/2005 | Blersch |
| 6,910,884 B2 | 6/2005 | Kelly et al. |
| 6,913,459 B2 | 7/2005 | Fukutomi |
| 7,001,179 B2 | 2/2006 | Devincenzo |
| 7,025,591 B1 | 4/2006 | Kesling |
| 7,033,170 B2 | 4/2006 | Cordato |
| 7,033,171 B2 | 4/2006 | Wilkerson |
| 7,055,908 B1 | 6/2006 | Williams |
| 7,074,037 B2 | 7/2006 | Macchi |
| 7,094,052 B2 | 8/2006 | Abels et al. |
| 7,140,875 B2 | 11/2006 | Lai et al. |
| 7,151,541 B2 | 12/2006 | Seder |
| 7,153,130 B2 | 12/2006 | Christoff |
| 7,210,927 B2 | 5/2007 | Abels et al. |
| 7,234,935 B2 | 6/2007 | Abels et al. |
| 7,247,018 B2 | 7/2007 | Freeman et al. |
| 7,258,545 B2 | 8/2007 | Hotta |
| 7,267,545 B2 | 9/2007 | Oda |
| 7,306,458 B1 | 12/2007 | Lu |
| 7,416,408 B2 | 8/2008 | Farzin-Nia et al. |
| 7,621,743 B2 | 11/2009 | Bathen et al. |

(56) References Cited

U.S. PATENT DOCUMENTS

| | | |
|---|---|---|
| 7,695,277 B1 | 4/2010 | Stevens |
| 7,704,072 B2 | 4/2010 | Damon |
| 7,780,443 B2 | 8/2010 | Hagelganz |
| 7,811,087 B2 | 10/2010 | Wiechmann et al. |
| 7,850,451 B2 | 12/2010 | Wiechmann et al. |
| 7,909,603 B2 | 3/2011 | Oda |
| 7,959,437 B2 | 6/2011 | Zakhem |
| 7,963,768 B2 | 6/2011 | Hilliard |
| 8,251,697 B2 | 8/2012 | Smith et al. |
| 8,376,739 B2 | 2/2013 | Dupray et al. |
| 8,485,816 B2 | 7/2013 | Macchi |
| 8,573,971 B2 | 11/2013 | Stevens |
| 8,585,399 B2 | 11/2013 | Smith et al. |
| 8,678,818 B2 | 3/2014 | Dupray et al. |
| 8,807,997 B2 | 8/2014 | Smith et al. |
| 8,961,172 B2 | 2/2015 | Dupray et al. |
| 8,979,528 B2 | 3/2015 | Macchi et al. |
| 9,144,473 B2 | 9/2015 | Aldo |
| 2001/0036615 A1 | 11/2001 | Binder |
| 2002/0025502 A1 | 2/2002 | Williams |
| 2002/0110778 A1 | 8/2002 | Abels et al. |
| 2002/0187452 A1 | 12/2002 | Abels et al. |
| 2003/0049582 A1 | 3/2003 | Abels et al. |
| 2003/0064344 A1 | 4/2003 | Vazquez |
| 2003/0088261 A1 | 5/2003 | Schraga |
| 2003/0096209 A1 | 5/2003 | Sugiyama et al. |
| 2003/0143509 A1 | 7/2003 | Kopelman et al. |
| 2004/0244149 A1 | 12/2004 | Anscher |
| 2004/0259048 A1 | 12/2004 | Balabanovsky |
| 2005/0069833 A1 | 3/2005 | Chikami |
| 2005/0244777 A1 | 11/2005 | Schultz |
| 2006/0014116 A1 | 1/2006 | Maijer et al. |
| 2006/0046224 A1 | 3/2006 | Sondhi et al. |
| 2006/0063123 A1 | 3/2006 | Cleary et al. |
| 2006/0099544 A1 | 5/2006 | Lai et al. |
| 2006/0099545 A1 | 5/2006 | Lai et al. |
| 2006/0172251 A1 | 8/2006 | Voudouris |
| 2006/0199137 A1 | 9/2006 | Abels et al. |
| 2006/0228662 A1 | 10/2006 | Lokar et al. |
| 2006/0228664 A1 | 10/2006 | Castner et al. |
| 2006/0246392 A1 | 11/2006 | Vigolo |
| 2006/0252002 A1 | 11/2006 | Hanson |
| 2006/0257810 A1 | 11/2006 | Maijer et al. |
| 2006/0263737 A1 | 11/2006 | Oda |
| 2006/0269889 A1 | 11/2006 | Voudouris |
| 2007/0054231 A1 | 3/2007 | Manemann et al. |
| 2007/0092849 A1 | 4/2007 | Cosse |
| 2007/0166658 A1 | 7/2007 | Voudouris |
| 2007/0172112 A1* | 7/2007 | Paley ............... A61B 5/4547 382/154 |
| 2007/0207436 A1 | 9/2007 | Tan et al. |
| 2007/0224569 A1 | 9/2007 | Oda |
| 2007/0243497 A1 | 10/2007 | Voudouris |
| 2007/0248926 A1 | 10/2007 | Lai et al. |
| 2007/0256694 A1 | 11/2007 | Kussick |
| 2007/0259301 A1 | 11/2007 | Hagelganz et al. |
| 2007/0264606 A1 | 11/2007 | Muha |
| 2007/0281269 A1 | 12/2007 | Forster |
| 2008/0014544 A1 | 1/2008 | Nucera |
| 2008/0128297 A1 | 6/2008 | Rose |
| 2008/0131831 A1 | 6/2008 | Abels et al. |
| 2008/0138759 A1 | 6/2008 | Kravitz et al. |
| 2008/0160474 A1 | 7/2008 | Wolf et al. |
| 2008/0182219 A1 | 7/2008 | Spalty |
| 2008/0223377 A1 | 9/2008 | Kussick |
| 2008/0227047 A1 | 9/2008 | Lowe et al. |
| 2008/0268398 A1 | 10/2008 | Cantarella |
| 2009/0004617 A1 | 1/2009 | Oda et al. |
| 2009/0004618 A1 | 1/2009 | Oda et al. |
| 2009/0004619 A1 | 1/2009 | Oda et al. |
| 2009/0042160 A1 | 2/2009 | Ofir |
| 2009/0162807 A1 | 6/2009 | Hagelganz et al. |
| 2009/0291404 A1 | 11/2009 | Oda |
| 2009/0325118 A1 | 12/2009 | Lewis et al. |
| 2010/0003632 A1 | 1/2010 | Ruiz Diaz et al. |
| 2010/0062387 A1 | 3/2010 | Hilliard |
| 2010/0129765 A1 | 5/2010 | Mohr et al. |
| 2010/0159411 A1 | 6/2010 | Oda |
| 2010/0178629 A1 | 7/2010 | Oda et al. |
| 2010/0196840 A1 | 8/2010 | Lai et al. |
| 2010/0203463 A1 | 8/2010 | Huff et al. |
| 2010/0261131 A1 | 10/2010 | Ruiz-Vela et al. |
| 2010/0279247 A1 | 11/2010 | Kesling |
| 2010/0285420 A1 | 11/2010 | Oda |
| 2010/0285421 A1 | 11/2010 | Heiser |
| 2010/0304321 A1 | 12/2010 | Patel |
| 2011/0014583 A1 | 1/2011 | Romano et al. |
| 2011/0020762 A1 | 1/2011 | Kanomi et al. |
| 2011/0039224 A1 | 2/2011 | Cosse |
| 2011/0076633 A1 | 3/2011 | Bryant |
| 2011/0081622 A1 | 4/2011 | Mashouf |
| 2011/0086322 A1 | 4/2011 | Baron et al. |
| 2011/0123942 A1 | 5/2011 | Rudman et al. |
| 2011/0165532 A1 | 7/2011 | Benvegnu' et al. |
| 2011/0287378 A1 | 11/2011 | Dupray et al. |
| 2012/0070797 A1 | 3/2012 | Edgren |
| 2013/0280668 A1 | 10/2013 | Upchurch, Jr. et al. |
| 2013/0280670 A1 | 10/2013 | Edgren |
| 2013/0309624 A1 | 11/2013 | Smith et al. |
| 2014/0356801 A1 | 12/2014 | Smith et al. |
| 2015/0173858 A1 | 6/2015 | Dupray et al. |
| 2015/0182304 A1 | 7/2015 | Gualano |

FOREIGN PATENT DOCUMENTS

| | | |
|---|---|---|
| EP | 0317098 | 5/1989 |
| EP | 0379668 | 8/1990 |
| EP | 0389223 | 9/1990 |
| EP | 0397533 | 11/1990 |
| EP | 0588961 | 3/1994 |
| EP | 0624354 | 11/1994 |
| EP | 0875211 | 11/1998 |
| EP | 1332727 | 8/2003 |
| EP | 1359859 | 11/2003 |
| ES | 2130174 | 7/1999 |
| FR | 2497657 | 7/1982 |
| FR | 2887135 | 12/2006 |
| JP | S60-113016 | 7/1985 |
| JP | S64-25847 | 1/1989 |
| JP | H01-160547 | 6/1989 |
| JP | H02-147112 | 12/1990 |
| JP | H03-21236 | 1/1991 |
| JP | H06-507803 | 9/1994 |
| JP | 2579431 | 2/1997 |
| JP | 11-276504 | 10/1999 |
| JP | 2003-102749 | 4/2003 |
| JP | 2009-535160 | 10/2009 |
| JP | U3155836 | 11/2009 |
| WO | WO 91/07925 | 6/1991 |
| WO | WO 92/00041 | 1/1992 |
| WO | WO 92/20296 | 11/1992 |
| WO | WO 2004/039276 | 5/2004 |

OTHER PUBLICATIONS

U.S. Appl. No. 11/123,470, filed May 5, 2005, Wilson.
U.S. Appl. No. 13/199,828, filed Sep. 9, 2011, Rudman et al.
U.S. Appl. No. 13/506,513, filed Apr. 23, 2012, Rudman et al.
U.S. Appl. No. 14/860,028, filed Sep. 21, 2015, Macchi.
3M Unitek Corporation Catalog, 1990, pp. 1-1, 1-3, 3-7, Figs. A, B.
"Buccal Tube," Sankin, printed Apr. 1, 2004, 7 pages.
"Direct Bond Tubes," American Orthodontics, New Products Catalog, 2006, p. 76.
"Focus on Brackets," Orthodontic Products, Mar. 2005, pp. 1-2.
Ortho Organizers, Inc. Advertisement, "Journal of Clinical Orthodontics," Sep. 1989, 3 pages.
Victory Series Appliance System, Mastering the Art of Orthodontic Application, 3M Unitek Dental Products Division, 1998, 4 pages.
Epstein, "Bi-Dimensional Orthos Treatment: Benefits and Rationale of Differential Bracket-Slot Sizes," Clinical Impressions, 1998, vol. 7(3), 6 pages.

(56) References Cited

OTHER PUBLICATIONS

Ricketts, "Provocations and Perceptions in Cranio-Facial Orthopedics," RMO, Inc., Denver, CO, USA, 1989, cover and pp. 982-1021.

* cited by examiner

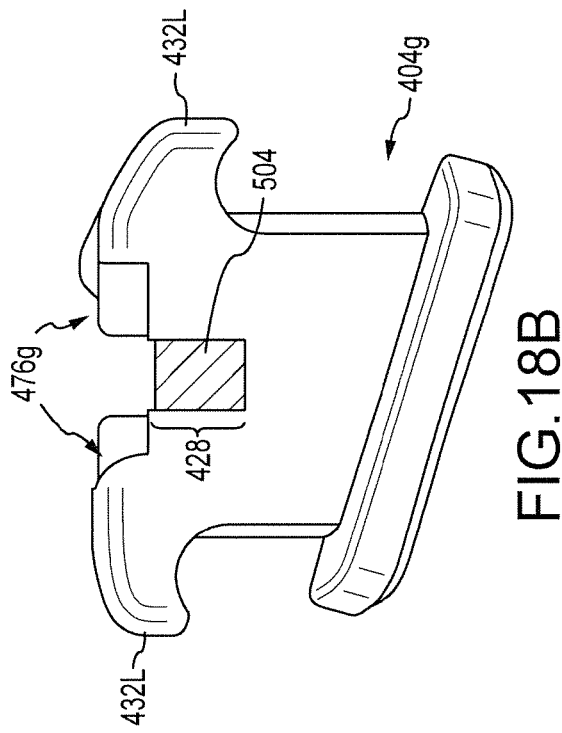
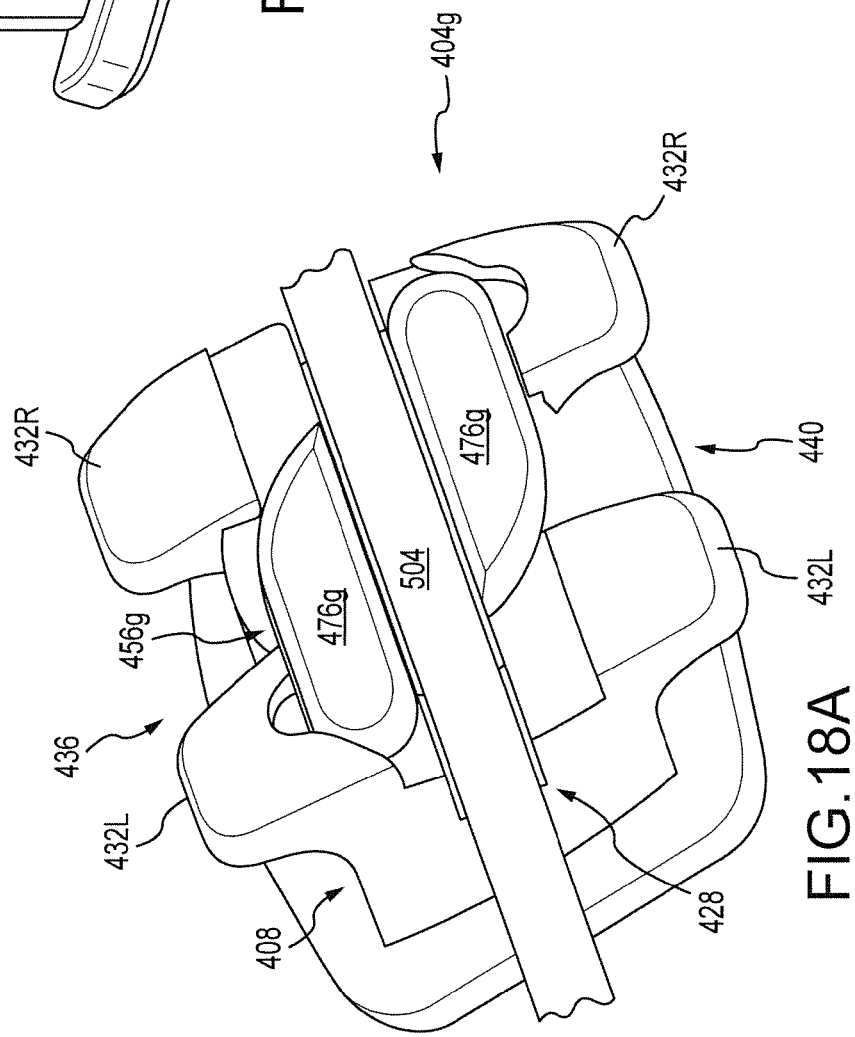
FIG. 18B
FIG. 18A

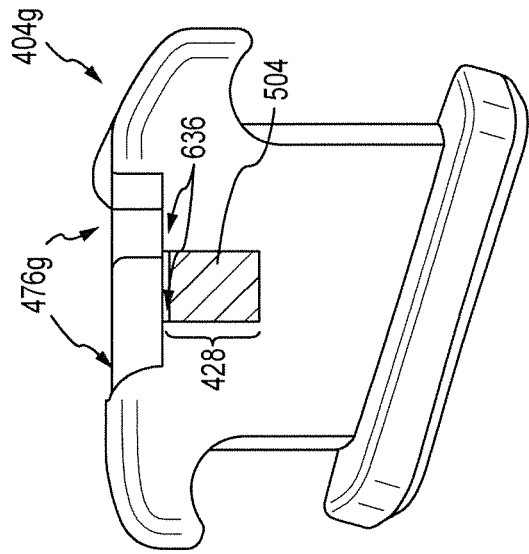
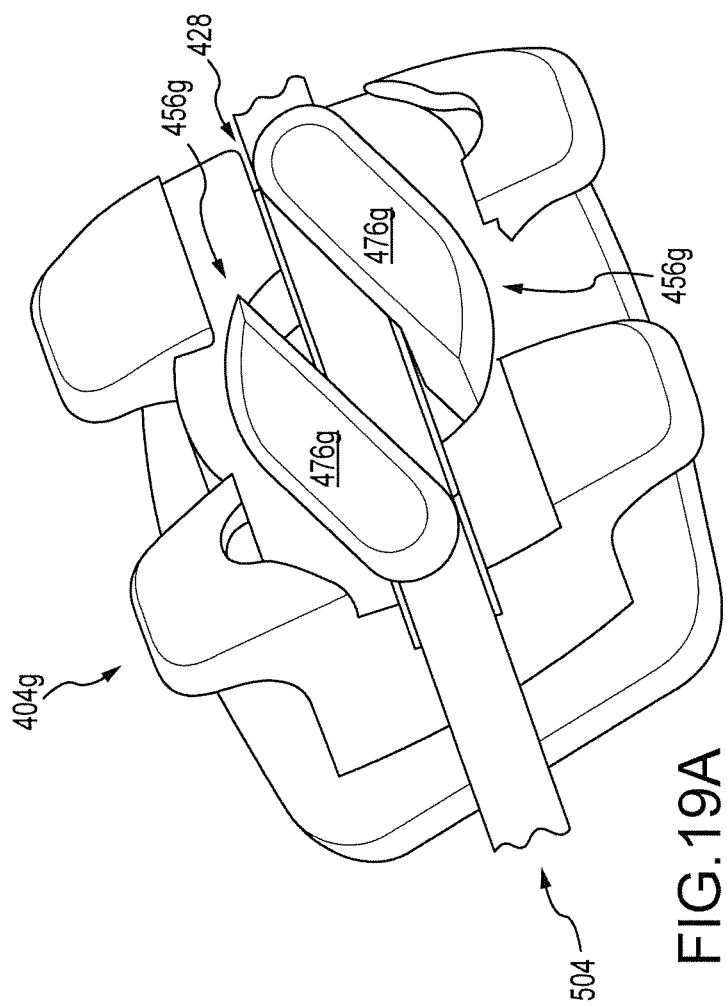
FIG. 19B
FIG. 19A

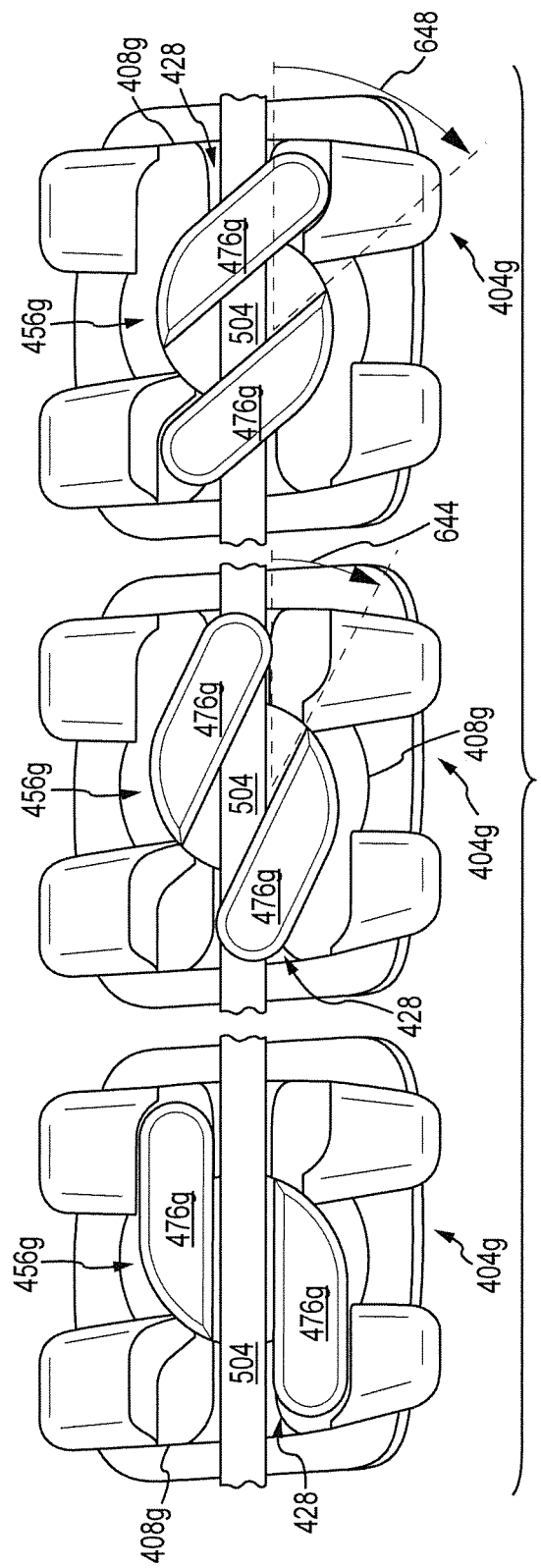

METHOD FOR PRODUCING A CUSTOMIZED ORTHODONTIC APPLIANCE

REFERENCE TO RELATED APPLICATIONS

This application is a continuation of U.S. patent application Ser. No. 13/762,455, filed on Feb. 8, 2013, which is a continuation-in-part application to and claims priority to U.S. patent application Ser. No. 13/117,085, filed May 26, 2011 (now U.S. Pat. No. 8,376,739, issued Feb. 19, 2013), which claims priority to U.S. Provisional Patent Application No. 61/518,927, filed May 12, 2011; both of which are incorporated fully herein by this reference. This application being a continuation of Ser. No. 13/762,455, filed on Feb. 8, 2013, which is a continuation-in-part application of U.S. patent application Ser. No. 12/937,588 filed on Dec. 15, 2010 (now U.S. Pat. No. 8,371,847, issued Feb. 12, 2013); this application being a continuation of Ser. No. 13/762,455, which is a continuation-in-part of U.S. patent application Ser. No. 13/595,548, filed Aug. 27, 2012 (now U.S. Pat. No. 8,585,399, issued Nov. 19, 2013), which is a continuation of U.S. patent application Ser. No. 11/852,057, filed Sep. 7, 2007 (now issued U.S. Pat. No. 8,251,697, issued Aug. 28, 2012), and claims the benefit of U.S. Provisional Application No. 60/824,891 filed on Sep. 7, 2006; this application also seeks priority from U.S. patent application Ser. No. 12/724,159, filed Mar. 15, 2010 (now U.S. Pat. No. 8,485,816, issued Jul. 16, 2013, which claims the benefit of U.S. Provisional Patent Application Ser. No. 61/160,653, filed Mar. 16, 2009. The entire disclosure of the prior applications listed above are incorporated herein fully by reference.

FIELD OF THE INVENTION

The present disclosure is directed, at least in part, to a self ligating orthodontic bracket system where at least some of the brackets employed have a rotatable member for securing an archwire within a slot of the bracket, and particularly to a lingual system that incorporates the same.

BACKGROUND OF THE INVENTION

Orthodontic brackets are widely used to align teeth through the application of forces selectively provided by interconnected archwires and accessories. Brackets are typically of metal, ceramic or composite construction and are interconnected to either bands or bonding pads for attachment to teeth.

In edgewise brackets, an archwire passes through a labially opening, horizontal slot defined by one or more pair of opposing tie wings. The archwire is preshaped and sized to provide the desired forces. In each bracket, a tie wing pair includes a gingivally extending tie wing and occlusally extending tie wing. Once placed in the slot of one or more pair of tie wings, an archwire is typically restricted therein by a ligating device such as a steel or elastomeric ligature.

As orthodontic treatment objectives and techniques continue to evolve, numerous corresponding edgewise bracket designs and interconnecting accessories have been proposed. Recently, it has been recognized that it is desirable to reduce frictional engagement between the archwire and bracket surfaces defining the archwire slot to facilitate space closure and bodily tooth movement. Similarly, in many situations, it is now a goal to reduce frictional engagement between the archwire and ligating device employed to restrict the archwire within the slot. Such friction reduction can markedly increase the rate of tooth movement and reduce the duration of the orthodontic treatment.

At the same time, patient comfort and ease-of-use considerations have become increasingly important. Patient comfort has been largely addressed by reducing bracket size to yield smaller and more smoothly contoured brackets. Ease-of-use considerations have stimulated bracket designs which facilitate practitioner's bracket placement/use and accommodate plural modalities. Lingual orthodontic systems and brackets are desirable due to both aesthetic and certain functional desires, and having a lingual self-ligation bracket system is a long sought after objective, especially one with enhanced friction reducing features.

There is a growing segment of the population that desires a lingual based system in order to correct their teeth. Lingual braces are fastened to the insides, or lingual side, of a person's teeth and are thus hidden from view. Like traditional braces, lingual braces use a system of brackets and wires to apply continuous pressure to teeth, encouraging them to gradually shift into alignment. Such lingual based bracket systems have become popular among adults who want an improved smile without having to display to the public a mouthful of metal, typically associated with adolescence, the more conventional and typical period of life when teeth are straightened. The advent of self-ligating brackets opens up opportunities for the relatively recent expansion of lingual based bracket systems and there is a long-felt, but unsolved need for systems that incorporate a cost effective and easy way in which to facilitate lingual based systems.

SUMMARY OF THE INVENTION

Embodiments of the orthodontic bracket and bracket system disclosed herein include a bracket body containing the archwire slot as well as tie wings for attaching various orthodontic devices (e.g., elastomeric bands) to the bracket. The rotatable member is rotatable in a first direction (e.g., counter clockwise) relative to a body of the bracket for securing or locking the archwire within the slot, and for rotating in an opposite direction (e.g., a clockwise direction) relative to the bracket body for unsecuring or unlocking the archwire so that it is substantially unrestrained from exiting the slot.

The rotatable member may include a cylindrical or circular portion for inserting into and rotating within a cylindrical bore or recess within the bracket body, wherein the cylindrical recess may be positioned so that it spans the width of the bracket slot. The rotatable member may further include one or more slot coverable extensions of various shapes and functionality wherein such extensions can be rotated into the slot opening where an archwire can be inserted into the opening and/or removed from the bracket slot via this opening. In particular, such extensions, when rotated to occlude at least a portion of the slot opening thereby preventing an archwire residing in the bracket slot from exiting therefrom, and when rotated out of the slot opening, these extensions do not prevent the archwire from being readily removed from the bracket slot, e.g., by an orthodontist or technician. In one or more embodiments, such coverable extensions may be C-shaped. However, other shapes are also within the scope of the present disclosure. In particular, such slot coverable extensions may be straight or bar shaped, such extensions may be parallel to one another, or such extensions may be generally irregularly shaped. Additionally, such extensions may include one or more notches that can be assessed by an orthodontic tool for rotating the rotatable member.

In one or more embodiments, the rotatable member may include two opposing columns attached to opposing sides of the circumference of the cylindrical portion, wherein such columns extend away from their attachment to the cylindrical portion such that they extend out of the cylindrical recess for attaching to the one or more rotatable extensions described above. The attachment of the columns to opposing sides of the cylindrical portion allow for the insertion of an archwire between the columns so that the archwire can reside in the archwire slot. More specifically, although the columns extend above the side walls of the slot, the columns do not interfere, regardless of the rotation of the rotatable member (relative to the bracket body), with an archwire's placement in or removal from the archwire slot. In particular, the columns may rotate (when the rotatable member rotates) about a central axis of the cylindrical recess, and rotate within a confined angular range that prevents them from conflicting or interfering with the operation of an archwire within the slot.

In one or more embodiments, the rotatable member and the cylindrical recess may include various features for being rotatably securing the rotatable member within the cylindrical recess so that this member is substantially prevented for disengaging from the bracket body. Such features may include mating combinations of projections and recesses such that a projection (or recess) may be provided on the cylindrical portion and/or the columns for mating with a corresponding recess (or projection) of an interior wall of the cylindrical recess for locking the rotatable member therein while also allowing it to rotate therein. Note that such mating projections and recesses may be, respectively, ridges and grooves.

Also, note that the cylindrical recess may include additional features or mechanisms that prevent the rotatable member from freely rotating within the cylindrical recess. In one or more embodiments, a circular cross section (perpendicular to the central axis of the cylindrical recess) may be slightly out of round in various places to frictionally engage adjacent surfaces of the rotatable member for assisting in maintaining the slot coverable extensions in one or more predetermined orientations relative to the slot. In one or more embodiments of the bracket, the cylindrical recess and the rotatable member may include interlocking elements that substantially restrict the rotation of the rotatable member to discrete and predetermined angular orientations about the central axis. Such interlocking elements may provide a ratchet mechanism, or alternatively interlocking shapes wherein a first shaped element (e.g., on the cylindrical portion of the rotatable member or a wall portion of the cylindrical recess) mates or interlocks with compatibly one or more shaped elements (on the other of the rotatable member or a wall of the cylindrical recess) dispersed at discrete angular positions about the central axis for restricting rotation of the rotatable member from one of these positions to another. Note that such interlocking elements may allow the rotatable member to rotate in both a clockwise and a counter clockwise direction when a sufficient predetermined directional force(s) is applied for disengaging the interlocking elements from a first position and interlocking at a second position.

In one or more embodiments of the bracket, the strength transmitted to the free ends of the slot coverable extensions for covering the slot is partially derived from the circular shape of the attached cylindrical portion and the intimate fitting of this cylindrical portion of the rotatable member within the cylindrical recess. In particular, such strength may allow the extensions to be thinner than one of ordinary skill in the art would expect, thus providing additional patient comfort.

In one or more embodiments of the slot coverable extensions, the side thereof facing the bracket body may include features or elements for engaging with the bracket body adjacent the slot for assisting in holding such extensions in a "closed" position (i.e., where the extensions span or at least partially cover a width of the slot opening thereby preventing, e.g., an archwire from exiting the slot), or in an "open" position (i.e., where the extensions do not span or interfere with the slot opening in a manner that would prevent an archwire from entering or exiting the slot). In particular, such an underside may include one or more protrusions for mating with a corresponding depression in the bracket body adjacent the slot.

In one or more embodiments, the bracket's cylindrical recess remains open (e.g., not completely enclosed) to facilitate self cleaning, and to reduce calculus build up and stuck moving parts. In another embodiment, the bracket's cylindrical recess is completely enclosed. Tooth brush bristles can access the walls of bracket body.

In one or more embodiments of the bracket, the slot coverable extensions can be configured so that in at least one rotatable position such extensions cause or induce an archwire in the slot to be "actively" held in place within the slot, wherein, for example, the extensions (or another bracket component) contacts the archwire for causing or forcing the archwire into contact with the surfaces of the slot (e.g., a floor of the slot) with sufficient force to induce frictional forces there between such that (for orthodontic purposes) such frictional forces effectively inhibit movement of the archwire in a direction along the length of the slot. Additionally/alternatively, the slot coverable extensions can be configured so that in at least one rotatable position such extensions cause or induce an archwire in the slot to be "passively" held in place within the slot, wherein, for example, the extensions (or another bracket component) only loosely restrains the archwire to remain in the slot in a manner such that the archwire can readily move in a direction along the length of the slot. In particular, in the passive archwire restraining configuration, there is insufficient frictional forces between the archwire and the slot (for orthodontic purposes) to effectively inhibit movement of the archwire in a direction along the length of the slot. Moreover, in one or more embodiments of the bracket, the slot coverable extensions can be rotated from a passive configuration to an active configuration, and/or from an active configuration to a passive configuration.

The orthodontic bracket disclosed herein may be comprised of metal, plastic or ceramic or combinations thereof. Equivalent materials also may be used. Metal injection molding (MIM) technology can be used for manufacturing components of the bracket, including the bracket body which provides features for rotatably securing the rotatable member to this body. In particular, the bracket body may be manufactured using a breakaway design in MIM for one piece bracket body assembly.

Still other embodiments are included within the scope of the present disclosure. For example, in one embodiment, rotating portions reversibly secure an archwire in the slot and rotate between a freely rotating position and a reversibly anchored position. In one embodiment the anchored position involves a separate vertical or lateral movement of the rotating portion with respect to the remainder of the bracket so as to achieve a locking function. In other embodiments, at least two pivot pins are employed, each positioned one opposite side of the bracket, and in one embodiment, on different sides of the archwire slot. Still other embodiments involve rotation of a pivot pin having a pivot axis that is oriented in a non-perpendicular orientation to the archwire slot and/or in a position that is not substantially normal to the tooth surface.

In still other embodiments, the self-ligating orthodontic bracket includes a bracket body with an archwire slot, at least two, but in other embodiments four or more, spaced apart mounting arms having mounting slots, and a mounting pin permanently or removably mounted in the mounting slots. A closure member may be mounted to the body of the bracket and movable between a reversibly closed position in which at least a portion of the archwire slot is covered and an open position, in which the archwire slot is uncovered. The closure member may have various elements that slide, rotate, pivot, and/or enclose that can be mounted to the body of the bracket.

Yet another embodiment provides a self-ligating orthodontic bracket that includes a mounting base for attachment to a tooth surface, an archwire slot formed upon the base and sized for receiving an orthodontic archwire, a rotary ligating cover selectively rotatable between an open position permitting access to the archwire slot and a closed position covering the archwire slot, and one or more locking features for holding the rotary cover in a closed position. Such locking feature may be positioned and designed to cooperatively mate with other designated portions of the bracket so as to achieve desired reversible engagement and open-retention features may also be provided that facilitate the purposeful opening of the locking feature to permit manipulation of the bracket, archwire, etc. as deemed appropriate by either the orthodontist or the patient.

Other embodiments are directed towards an orthodontic self-ligating bracket provided with a cover that can be rotated over an arch wire slot in the base portion to close when a frangible portion is severed upon initiating rotation of the cover. Such cover rotates about a hinge, which may include a pin or axle that can be moved laterally and/or vertically after the frangible portion is severed and preferably is manufactured to form one piece, such as using an injection molding, machining, or casting process, thus avoiding additional subsequent assembly to attach a cover to a base.

Some embodiments employ a self-ligating orthodontic bracket clip slidably engagable with the bracket to allow the clip to slidably move between an open position and a closed position in which the clip extends across the archwire slot to retain the archwire in the archwire slot.

Other embodiments employ a replaceable closing spring member detachably connected to a base member to maintain pivoting engagement of such spring member when desired and easy removal of the spring members when desired.

Other self ligating bracket designs include a latching member having a hinge pin made of a flexible material so that a portion of the latching member is engagable with the bracket.

In some embodiments, a range of adjustability is provided in the range of motion of a closing or locking member, thus limiting the forces encountered by an archwire held in the archwire slot, thus permitted desired sliding of the archwire in the slot. To accomplish this end, a camming mechanism can be employed. The bracket body may be formed from a non-metallic material, such as a polymer, a filled polymer composite, or a ceramic, and the self-ligating mechanism may be formed from a metal. A resilient engagement member with a detent positioned to engage an aperture can be employed to achieve secure closure.

To further an appreciation of the various designs of the present disclosure and to assist in providing requisite support of written description and enablement of the various features of the present disclosure, the following references are hereby incorporated herein by reference in their entries: 20110081622 to Mashouf; U.S. Pat. No. 7,695,277 to Stevens; 20100203463 to Huff; U.S. Pat. No. 7,780,443 to Hagelganz; 20110076633 to Bryant; 20100285421 to Heiser; 20100159411 to Oda; 20100062387 to Hilliard.

One aspect of the present invention is directed to lingual orthodontic systems and methods, and particularly those employing the rotatable, self-ligating brackets as described herein. For mainly aesthetic reasons, orthodontic appliances have been developed in which each bracket is fixed to a surface of the corresponding tooth that lies inside the mouth, on the palate side, of a patient, known as the lingual surface. On particular embodiment is directed to a lingual system that includes the use of the self-ligating rotatable brackets as described herein.

One concept generally employed in orthodontics relies on configuring the orthodontic archwire as a straight archwire. What a straight archwire is, is an archwire substantially in the shape of a flat U, a semi-elliptical shape or a parabolic shape, that is to say a flat regular curve positioned with respect to the dental arch parallel to the occlusal plane.

A straight archwire is not specific to a patient's dental arch and has a simple shape that can be produced easily and on an industrial scale, and therefore at low cost.

In the case of a dental arch that requires orthodontic treatment, a preformed straight archwire that has the desired shape of the dental arch at the end of treatment is used. When a predefined straight archwire is positioned on an orthodontic appliance in position on a dental arch, the straight archwire is partially deformed, within the elastic limits of the material of which the straight archwire is made, as they are inserted into the slot of each bracket. When the treatment is finished, the straight archwire will have returned to its initial shape because the teeth will have been moved under the effect of the forces exerted by the prestressed orthodontic archwire. In practice, a straight archwire has a rectangular, square or round cross section and its curvature is modified as the treatment progresses.

In a configuration such as this, because the orthodontic archwire is not specifically designed for a patient's dental arch, it is the brackets which are specially tailored to each one of a patient's teeth.

In order to design an orthodontic appliance tailored to each of a patient's teeth, one known method of designing and producing brackets is to produce an integral (bracket bonding pad and bracket body) bracket from numerical models of separate elements, one element representative of the bracket bonding pad and one element representative of the bracket body, and then numerically assemble them.

In order to achieve the production of a bracket, the method includes the steps of: numerically representing the dentition of the patient, formulating the bracket bonding pad of a bracket on the lingual face of the relevant tooth, in numerical form, selecting a numerical representation of a bracket body from a database, positioning the numerical representation of the selected numerical bracket body on the bracket bonding pad of the bracket.

The bracket thus designed is a numerical object corresponding to the merger of a number of three-dimensional objects (bracket bonding pad and bracket body) designed to suit, and containing customized designs for each of the patient's teeth.

The numerical object is then exported in the form of numerical files to a machine tool or the like intended to produce the bracket from a biocompatible material in accordance with the shape thus defined.

In this method of manufacturing a bracket, only the bracket bonding pad is designed numerically from the surface of the patient's tooth, the bracket body being taken from a database and firmly attached to the bracket bonding pad later.

The present invention proposes a method of producing a customized orthodontic appliance. An orthodontic appliance comprises: brackets fixed to teeth of a dental arch of a patient, each bracket being fixed to a surface of a tooth of the dental arch by a bracket bonding pad of the bracket, an orthodontic archwire fixed to the brackets in a housing of a bracket body of each bracket.

The method according to the invention includes a step of constructing a numerical representation of each bracket from a numerical representation of the desired end-of-treatment dental arch, known as the dental arch final numerical representation. According to the method, the step of constructing the numerical representation of each bracket comprises the steps of: a—positioning a numerical representation of the orthodontic archwire with respect to the dental arch final numerical representation, then b—for each tooth of the dental arch final numerical representation, positioning a numerical representation of a volume representative of an envelope volume of a bracket body, known as the second volume, of a bracket blank such that it interferes with the orthodontic archwire and in close proximity to the relevant tooth, and c—for each tooth of the dental arch final numerical representation, positioning a numerical representation of a volume representative of an envelope volume of a bracket bonding pad, known as the first volume, of the bracket blank such that it interferes with the second volume and with the volume of the relevant tooth, then, d—determining, for each tooth in the first volume and in the second volume, volumetric exclusion zones, which volumetric exclusion zones contain all of the volumes that interfere with the tooth for the first volume and all of the volumes that interfere with the orthodontic archwire for the second volume.

The numerical representation of the bracket of one tooth is then determined by the volume of the bracket blank minus the volumetric exclusion zones.

For preference, in order to minimize a thickness of the bracket, the volumetric exclusion zones of the first volume are defined in such a way as to determine a substantially constant thickness of the numerical representation of the bracket bonding pad.

Advantageously, the blank is chosen from a database comprising at least two models of numerical representation of blanks and is chosen in relation to the shape of the relevant tooth so as to minimize the volume of the exclusion zones while at the same time keeping a sufficient aerial contact between a bearing surface of the bracket bonding pad and the surface of the tooth.

In order to implement step a) of the method, the numerical representation of the orthodontic archwire is positioned in such a way that a distance d, for each tooth of the dental arch final numerical representation, between the numerical representation of the orthodontic archwire and the surface of each tooth is greater than a minimum distance d.sub.min that corresponds to a minimum thickness of the numerical representation of the brackets at their bracket bodies.

In one embodiment of step b) of the method, for each tooth of the dental arch final numerical representation, the numerical representation of the second volume is positioned in such a way that a reference point of the second volume corresponds to a point of intersection between the numerical representation of the orthodontic archwire and an orthogonal projection of a centre of the relevant tooth.

In order for the orthodontic archwire to be able to slide naturally along the dental arch in the housings in the brackets as the teeth of the dental arch move, housings are produced, for certain sectors of the dental arch, with a cross section appreciably larger than a cross section of the orthodontic archwire.

For preference, the method is described in an application in which the orthodontic archwire is a flat orthodontic archwire because the forces applied by such flat archwires are those best suited both to the buccal physiology and to standardization of the treatment.

Without implying any restriction, the method is implemented using numerical representations of brackets positioned on either lingual or vestibular surfaces of the teeth of the dental arch final numerical representation.

Depending on the tooth considered, for example in the case of the incisors or the canines, the exclusion zones of the second volume determine a housing in the form of an open slot in the numerical representation of the bracket body to accommodate the numerical representation of the orthodontic archwire and, if appropriate, a numerical representation of orthodontic archwire self-ligating means. In the case of the terminal teeth in the dental arch of relevance to the orthodontic appliance, the exclusion zones of the second volume determine a housing in the form of a tube in the numerical representation of the bracket body to accommodate the numerical representation of the orthodontic archwire.

In one particular embodiment of the method, the method includes an additional step of determining volumetric exclusion zones in a numerical representation of at least one volume representative of an envelope volume of an ancillary accessory, known as a third volume, of the bracket blank, then a step of subtracting the volumetric exclusion zones from the blank in order to produce the ancillary accessory, such as a hook or a button for example.

For preference, the final numerical representation of the dental arch desired at the end of the treatment of the patient is produced from a numerical representation of the dental arch of the patient prior to treatment.

Once the construction step has been completed, the brackets are produced from a biocompatible material, for example by machining, in accordance with the numerical representations.

The invention also relates to a blank for the manufacture of a bracket of an orthodontic appliance, the bracket comprising a bracket bonding pad, closely applied to a surface of a patient's tooth, and a bracket body comprising a housing to accommodate an orthodontic archwire, the blank comprising at least two imbricated volumes constituting an envelope of at least two elements that are to be produced, one volume representative of an envelope volume of the bracket bonding pad, known as the first volume, and one volume representative of an envelope volume of a bracket body, known as the second volume.

In a preferred embodiment, the second volume is substantially spherical and located on the blank on an opposite side of the first volume to a side situated against the tooth.

In one shape example, in the lingual technique, the first volume is a convex body on the tooth side, for example in the case of the canines or incisors, and is a concave body on the tooth side, for example in the case of the premolars or molars.

Other embodiments include an orthodontic appliance includes features for reducing friction between an interior of an archwire slot portion of the appliance and an archwire to be placed within the archwire slot. Still other embodiments include a self ligating orthodontic bracket having a rotatable member for securing an archwire within a slot of the bracket, with a series of such brackets placed on bonding pads on the lingual side of a patient's mouth.

Various embodiments are set forth and described herein, including the following: In one embodiment, an orthodontic bracket system includes at least two brackets, each having a body having a front and a back, the back for facing a tooth when the bracket is operably attached thereto, and the front having at least one archwire slot therein, the slot having a length with at least a bottom, opposing sides, and an opening for providing an archwire therein, wherein the opening extends the length. A rotatable member is provided for rotating relative to the body from an open position wherein the opening provides archwire access to operably position the archwire within the at least one archwire slot, to at least one closed position wherein for each of the at least one closed position, at least a portion of the rotatable member inhibits the archwire from moving through the opening. A first portion of the rotatable member is secured within a recess of the body, and rotates therein when the rotatable member rotates between the open position and the at least one closed positions. The first portion includes at least one tab, and the recess includes a wall therein having a ledge, wherein the ledge and the at least one tab interact for preventing the first portion from detaching from the recess. Upon rotation of the rotatable member, the first portion contacts predetermined discrete notches within the recess for positioning the rotatable member at corresponding predetermined angular orientations about an axis of rotation through the body. The rotatable member includes a slot cover external to the body so that in the open position the slot cover provides archwire access for positioning the archwire within the at least one archwire slot, and in the at least one closed position the cover inhibits the archwire from moving through the opening. The slot cover comprises two slot coverable extensions that are substantially straight and bar shaped. When in an open position, the two slot coverable extensions are aligned parallel to each other and parallel to the opposing sides of the at least one archwire slot, with a gap between the slot coverable extensions to allow an archwire to be passed therethrough. The rotatable member has an axis of rotation extending substantially directly beneath the at least one archwire slot such that the axis of rotation of the rotatable member extends directly below and perpendicular to a longitudinal axis of the archwire when the archwire is positioned within the at least one archwire slot. The archwire is positioned between the two slot coverable extension when in the open position and is restrained by the two slot coverable extensions when in the at least one closed position. There are preferably from two to four notches formed in the first portion. The rotatable member has at least one gap formed in the first portion.

In a preferred embodiment of a ligual based bracket system that facilitates a self-ligating bracket to be employed, each bracket is fixed to a surface of a tooth by a bracket bonding pad.

Other aspects of the present invention are directed to a method of producing a customized orthodontic appliance that comprises the orthodontic bracket system that includes the self-ligating rotatable brackets as described herein. In one embodiment of such a method, a first step includes constructing, by a processing device, a numerical representation of each bracket from a dental arch final numerical representation. The numerical representation is positioned on an orthodontic archwire such that for each tooth of the dental arch final numerical representation, one also positions a second volume of a bracket blank, which includes a numerical representation of a volume representative of an envelope volume of a bracket body. This is done in a manner such that it interferes with the orthodontic archwire and is in close proximity to the relevant tooth. For each tooth of the dental arch final numerical representation, one then performs the step of positioning a first volume of the bracket blank, which includes a numerical representation of a volume representative of an envelope volume of a bracket bonding pad, such that it interferes with the second volume and with the volume of the relevant tooth. One then determines for each tooth in the first volume and in the second volume, volumetric exclusion zones, which contain all of the volumes that interfere with the tooth for the first volume and all of the volumes that interfere with the orthodontic archwire for the second volume. The numerical representation of the bracket of one tooth is determined by the volume of the bracket blank minus the volumetric exclusion zones. The volumetric exclusion zones of the first volume are defined in such a way as to determine a substantially constant thickness of the numerical representation of the bracket bonding pad. The blank is chosen from a database comprising at least two models of a numerical representation blank. The numerical representation blank is chosen in relation to the shape of the relevant tooth so as to minimize the volume of the exclusion zones while at the same time keeping a sufficient aerial contact between a bearing surface of the bracket bonding pad and the surface of the tooth.

In still other embodiments, the orthodontic bracket system includes at least one of the rotatable, self ligating brackets described herein, coupled with a base having a substantially uniform thickness and with at least one archwire tube connected to said base. The archwire tube preferably includes (i) a first aperture, (ii) a second aperture, and (iii) a passageway having a length between said first and second apertures, with the passageway adapted for receiving the archwire. The passageway comprises interior sides (namely a gingival side, an occlusal side, a lingual side and a buccal side) and preferably the buccal side comprises a friction reducing feature, and more preferably at least one of the group consisting of the gingival side, the occlusal side and the lingual side comprises a friction reducing feature. A first friction reducing features may include a projection extending substantially the length of said passageway and may extend into the passageway. The first friction reducing feature reduces contact of the archwire with a first predetermined portion of the passageway. A second friction reducing feature includes a plurality of separate projections residing along the length of said passageway, projecting into said passageway and spaced apart from each other along the length of said passageway. The second of the friction reducing features reduce contact of the archwire with a second predetermined portion of the passageway.

Yet a further aspect of the present invention is directed to a method for adjusting a patient's tooth using an orthodontic appliance that preferably includes at least one of the self-ligating rotatable brackets as described herein. Such a method includes securing an orthodontic appliance to a patient's tooth, where the appliance preferably includes: (a) a tooth attachment side for attaching to a tooth, and an outer side for facing away from the tooth; (b) mesial and distal archwire retaining portions for retaining an archwire in a first archwire retaining channel, each of the mesial and distal archwire retaining portions having a corresponding recess for receiving the archwire; (c) a first retaining ridge for holding the archwire in the corresponding recesses, the first retaining ridge extending away from the tooth attachment side further than distal and mesial ends of the first archwire retaining channel; (d) second mesial and distal archwire retaining portions for retaining a second archwire in a second archwire retaining channel, each of the second mesial and distal archwire retaining portions having a corresponding additional recess for receiving the second archwire; (e) a first bridge extending between and fixedly connecting the mesial archwire retaining portion and the second mesial archwire retaining portion; (f) a second bridge extending between and fixedly connecting the distal archwire retaining portion and the second distal archwire retaining portion; and (g) wherein the each of the first and second bridges enclose a part of an archwire retention channel between the first and second archwire retaining channels; and providing the archwire in an open side along a length of the first archwire retaining channel for receiving the archwire in the first archwire retaining channel. One then applies a force to the archwire for inducing a predetermined second bow therein when the archwire enters the first archwire retaining channel. The mesial and distal archwire retaining portions are on a first side of the first archwire retaining channel, and the first retaining ridge is on an opposing second side of the first archwire retaining channel. The archwire is thus contacted at a location between the mesial and distal archwire retaining portions for providing the predetermined bow in the archwire in a direction toward the first side. One then provides a second archwire in an open side along a length of the second archwire retaining channel for receiving the archwire in the second archwire retaining channel. Then a force is applied to the second archwire for inducing a predetermined bow therein when the second archwire enters the second archwire retaining channel. The second mesial and second distal archwire retaining portions are on a first side of the second archwire retaining channel, and a second retaining ridge is on an opposing second side of the second archwire retaining channel, contacting the second archwire at a location between the second mesial and second distal archwire retaining portions to provide a predetermined second bow in the second archwire in a direction toward the first side of the second archwire retaining channel.

Embodiments of the present disclosure are set forth in the attached figures and in the detailed description as provided herein and as embodied by the claims. It should be understood, however, that this Summary section may not contain all of the aspects and embodiments claimed herein. Additionally, the disclosure herein is not meant to be limiting or restrictive in any manner, and is directed to be understood by those of ordinary skill in the art. Moreover, the present disclosure is intended to encompass and include obvious improvements and modifications of embodiments presented herein.

Additional advantages of the present disclosure will become readily apparent from the following discussion, particularly when taken together with the accompanying drawings.

BRIEF DESCRIPTION OF THE DRAWINGS

A detailed description of the invention is given with reference to the figures which depict:

FIGS. 18A and 18B show views of a further embodiment of a self-ligating orthodontic bracket 404g with a slot covering rotatable member 456g, wherein this bracket is in the open configuration allowing easy insertion and/or extraction of an archwire 504 from the bracket slot 428. In particular, FIG. 18A shows a top (slightly oblique) view of the orthodontic bracket 404g, and FIG. 18B shows a corresponding side view of the bracket 404g.

FIGS. 19A and 19B show views of the self-ligating orthodontic bracket 404g, wherein this bracket is in the passively closed configuration such that insertion and/or extraction of an archwire 504 from the bracket slot 428 is prevented by rotatable member 456g. However, the archwire 504 is relatively loosely confined to the slot 428. In particular, FIG. 19A shows a top (slightly oblique) view of the orthodontic bracket 404g in the closed passive configuration, and FIG. 19B shows a corresponding side view of the bracket 404g.

FIG. 20A shows a top (slightly oblique) view of the orthodontic bracket 404g in the closed active configuration, and FIG. 2g0B shows a corresponding side view of the bracket 404g.

FIG. 21 shows a detailed end view of the slot 428 of the bracket 404g when the bracket is in the closed passive configuration.

DETAILED DESCRIPTION

Figure 1:
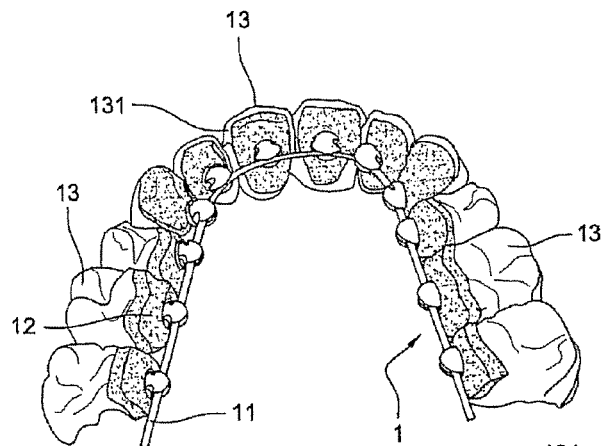
FIG. 1: a view, from the inside of the mouth, of a lingual orthodontic appliance on a dental arch of a patient.

An orthodontic appliance 1, designed for a dental arch, to correct defective positioning of the teeth of a dental system, comprises, as illustrated in FIG. 1, brackets 12, individually fixed to one tooth 13 each, and an orthodontic archwire 11 held in the brackets 12.

The example of an orthodontic appliance is illustrated and described in detail for brackets 12 positioned on surfaces of the teeth 13 that are located on the inside of the mouth, on the palate side, of a patient, known as the lingual surfaces 131. However, this choice is non-limiting and the brackets of the orthodontic appliance could equally be positioned on tooth surfaces situated on the lip side, and on the opposite side to said lingual surfaces, known as the vestibular surfaces.

A dental arch comprises various types of teeth, specifically incisors, canines, premolars and molars.

The orthodontic archwire is a preformed archwire, advantageously a flat archwire, that is to say an archwire situated substantially in one plane, and which has, in a relaxed (that is to say unstressed) position, the shape obtained when the desired shape of the dental arch at the end of treatment is obtained.

The exemplary embodiment of the invention is described in detail for a flat archwire.

The flat archwire is substantially U-shaped or semi-elliptical or parabolical, substantially parallel to the occlusal plane, and, for example, has a uniform flat curve, substantially level with the incisors and the canines, and two substantially straight lines extending from each end of the curve substantially level with the premolars and the molars so that it more or less represents the shape of a dental arch on the side on which the orthodontic archwire is fitted.

The flat orthodontic archwire has a variable cross section, such as, for example, a rectangular, square, circular or elliptical cross section. For the purposes of the illustrations, a rectangular cross section has been adopted.

Figure 2A:
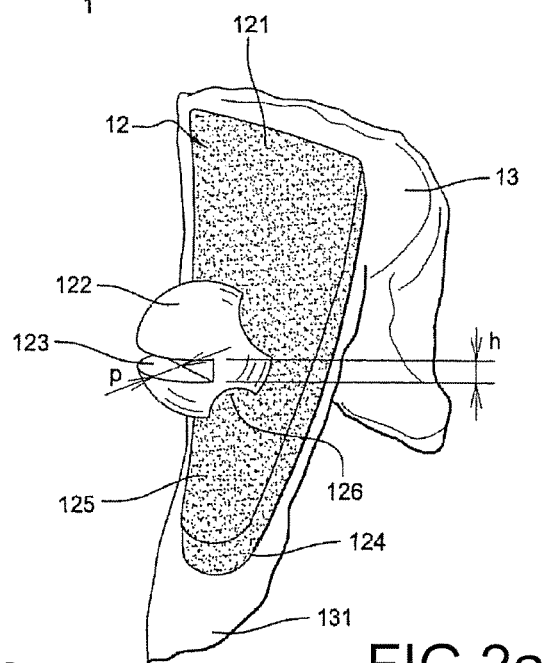
FIG. 2a: a perspective depiction of a bracket according to the invention attached to a surface of a tooth.

A bracket 12 comprises, as illustrated in FIG. 2a, a bracket bonding pad 121, closely following the lingual surface 131 of the tooth 13, and a bracket body 122, firmly attached to the bracket bonding pad, comprising a housing 123 tailored, in terms of shape and size, to accommodate the orthodontic archwire 11.

The bracket bonding pad comprises a bearing surface 124, facing the lingual surface 131 of the tooth 13, and which, in inverse relief, has a shape substantially identical to the lingual surface.

In a known way, the bracket bonding pad 121 is held on the lingual surface 131 of the tooth 13 using an adhesive cement (not depicted).

For preference, the bracket bonding pad has a relatively small thickness that is substantially constant and comprises a surface 125, on the opposite side to the bearing surface 124, that has a shape substantially parallel to the bearing surface 124.

This overall shape of the bracket 12 is particularly well suited to lingual orthodontics because it: reduces speech problems, reduces tongue irritation, is more comfortable for the patient, is more hygienic, bonds better, and allows for better positioning of the bracket for bonding and rebonding.

Each housing 123 has a height h and a depth p and is arranged substantially in a plane of the orthodontic archwire.

In one embodiment, the housing has a height substantially identical to a maximum thickness of the orthodontic archwire.

In another embodiment, the housing has a height appreciably greater than the maximum thickness of the orthodontic archwire so as to accommodate the archwire and, where appropriate, orthodontic archwire self-ligating means (not depicted) inserted into the housing.

The orthodontic archwire self-ligating means allow the orthodontic archwire to be kept in place in the housing 123 without the need to resort to additional ligatures. In one exemplary embodiment, the self-ligating means are positioned in the housing 123 and, for example, adopt the form of an anchoring cage. In another exemplary embodiment, the self-ligating means are positioned on the orthodontic archwire.

In one embodiment, a housing has a rectangular cross section substantially, by way of higher value, measuring 0.46.times.0.64 mm or 0.56.times.0.71 mm, these dimensions being substantially equivalent to two orthodontic archwire sizes actually in use in the production of orthodontic appliances.

Figure 2B:
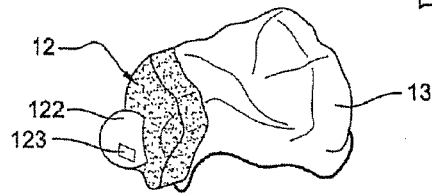
FIG. 2b: a perspective depiction of a bracket according to the invention attached to a surface of a tooth, and comprising a tube.

In a preferred embodiment, the housing 123 adopts the form of an open slot in the plane of the orthodontic archwire for the canines, the premolars and the molars, and adopts the form of a tube for the molars or other terminal teeth, as illustrated in FIGS. 1, 2a and 2b. In this embodiment, only the open slots contain the orthodontic archwire self-ligating means.

In one embodiment, in order to reduce friction and allow the orthodontic archwire 11 to slide naturally along the dental arch in the housings 123 of the brackets as the teeth 13 of the dental arch move, the orthodontic archwire has a cross section appreciably smaller than a cross section of the housings 123 of the brackets 12 in at least one sector of the dental arch.

In one exemplary embodiment, housings have variable cross sections along sectors of a dental arch in the case of an orthodontic archwire of constant square or rectangular cross section.

In another exemplary embodiment, the orthodontic archwire has a square or rectangular cross section that varies along sectors of dental arch in the case of housings of constant cross section, so as to encourage sliding mechanics during treatment.

This variable cross section of the housing 123 or of the orthodontic archwire 11 also improves control over the position and inclination of the orthodontic archwire in adjusted sections, and mechanical effectiveness in non-adjusted sections.

In order to reconcile better mechanical efficiency with a need for access for tooth-brushing, the housing 123 of the bracket 12 is preferably situated at a cervical limit of the tooth, that is to say as close as possible to the gum line and centred axially on the lingual surface 131 of the tooth 13.

In one embodiment, when the self-ligating means do not exist, the bracket body 122 has secondary slots 126, for example substantially parallel or perpendicular to the slot 123, to accommodate ligatures, for example of the metallic or elastomeric type, to hold the orthodontic archwire 11 in position in the slot of the bracket body, or auxiliary arch-wires.

For preference, the bracket body 122 has a rounded or at least blunted shape and has two diametrically opposed secondary slots to accommodate ligatures. For the description, use is made of bracket bodies of hemispherical shapes.

In one embodiment, to allow the treatment of complex disorders, for which the straightening afforded by the bracket 12 is insufficient, the bracket 12 comprises an ancillary accessory (not depicted) in relief, such as, for example, a button, a cleat, a spur or a hook which may be temporary or permanent.

When the ancillary accessory is permanent, the ancillary accessory is thinly attached to the bracket 12, either at the bracket bonding pad 121 or at the bracket body 122.

When the ancillary accessory is temporary, the bracket body 122 comprises a slit, for example substantially perpendicular to the housing and open-ended, to accept a fastener of the removable ancillary accessory.

For preference, the bracket 12 is produced from an appropriate material, such as stainless steel for example for its non-corrosive properties, or titanium.

In one particular embodiment, use is made of zirconium oxide which, for such an application, has advantages such as strength and colouring, so that it can be matched to the color of the teeth.

Figures 3A, 3B:
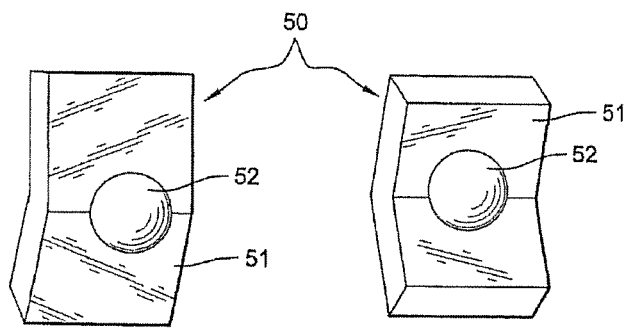
FIG. 3a: a perspective view of a first example of a blank for producing a bracket according to the invention.
FIG. 3b: a perspective view of a second example of a blank for producing a bracket according to the invention.

In order to produce a bracket 12 tailored to the specific shape of a patient's tooth 13, the method according to the invention consists in producing a bracket (bracket bonding pad and bracket body) from the conversion of a blank 50 such as the examples of blanks illustrated in FIGS. 3a and 3b.

The blank is determined by at least two imbricated volumes 51, 52 which constitute an envelope of the bracket that is to be produced. A first volume 51 is representative of an envelope of the bracket bonding pad 121 of the bracket 12. A second volume 52 is representative of an envelope volume of the bracket body 122 of the bracket 12. Advantageously, the second volume is embodied by a sphere corresponding to an envelope of the bracket body.

In the method, for the step of determining the shape of each bracket, recourse is had to numerical processing of the objects which are themselves represented in numerical form and which can, if need be, be represented graphically as illustrated by the figures. Unless otherwise mentioned and up to such point as the elements of the orthodontic appliance are physically embodied, the description should be understood to mean that each designated object (tooth, orthodontic archwire, bracket, ancillary accessory, etc.) means that numerical representation thereof, whether or not this has been visualized in graphical form, handled by computing means such as a computer. In particular, a suffix n associated with the reference numeral when referring to the figures, means that this is the numerical representation of the designated object.

According to the method, in a first step, a numerical representation of a patient's end-of-treatment dental arch is obtained and stored in a numerical memory. In one method for implementing this first step, the numerical representation is produced in two phases.

A first phase consists in storing a numerical representation, known as the initial numerical representation, of the patient's current dental arch in the numerical memory.

One way of implementing this first phase is, for example, to take an impression of the patient's dentition and then produce a model that will be scanned and converted, using, for example, a software package, into 3D numerical data in order to obtain an initial numerical representation of a dental arch of the current dentition.

Other ways of implementing this first phase are also conceivable, such as, for example, scanning the patient's dentition directly in three dimensions.

A second phase is to obtain a representation, known as the final numerical representation, of the desired end-of-treatment dental arch, from the initial representation.

This final numerical representation contains all of the teeth present at the end of the treatment, in their established arrangements and anatomical relationships.

One way of implementing this second phase is, for example, to use special purpose software that allows the teeth that were incorrectly positioned in the initial representation to be moved into a desired final position, for example 3D graphics software that allows an operator on a workstation fitted with a screen to manipulate each tooth in space.

Figures 4A, 4B:
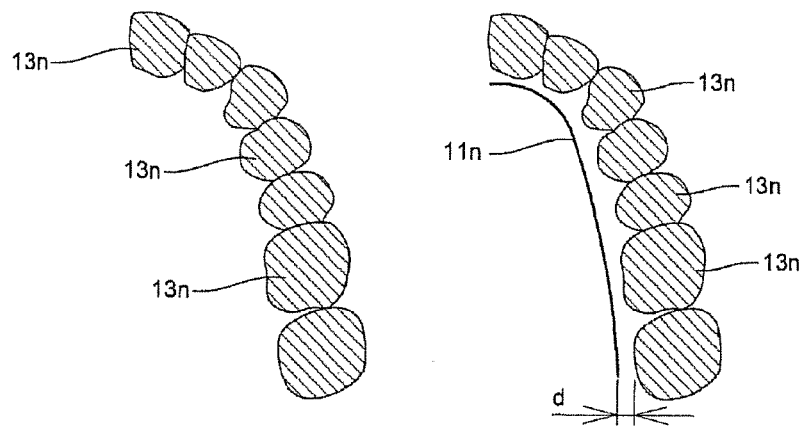
FIG. 4a: an illustration of a numerical representation of a cross section of a dental arch in a plane of the orthodontic archwire.
FIG. 4b: an illustration of a numerical representation of the positioning of an orthodontic archwire for a cross section of a dental arch in a plane of the orthodontic archwire, after a second step of the method.

In a second step of the method, as illustrated in FIGS. 4a and 4b, a flat orthodontic archwire 11n or a line characteristic of the orthodontic archwire, for example an axis, is positioned for the dental arch final numerical representation.

In a first phase, a plane of the orthodontic archwire is determined so that it is secant with the lingual surfaces of the teeth of the dental arch. The position of the plane, in terms of height and in terms of inclination of the orthodontic archwire, is chosen to suit clinical requirements, and preferably is chosen to lie substantially at a cervical limit of the tooth. FIG. 4a illustrates a cross section through the dental arch considered in the plane of the orthodontic archwire.

In a second phase, the orthodontic archwire 11n is constructed in such a way that the orthodontic archwire is determined by a continuous flat curve, which is substantially symmetric, of substantially parabolic outline and positioned such that a distance d, for each tooth of the dental arch, between the orthodontic archwire and the lingual surface 131n of each tooth 13n of the dental arch is greater than a minimum distance $d_{min}$ which depends, as appropriate, on the type of tooth considered, and that corresponds to a minimum thickness of the brackets 12n at their bracket body 122n.

Figures 5A, 5B:
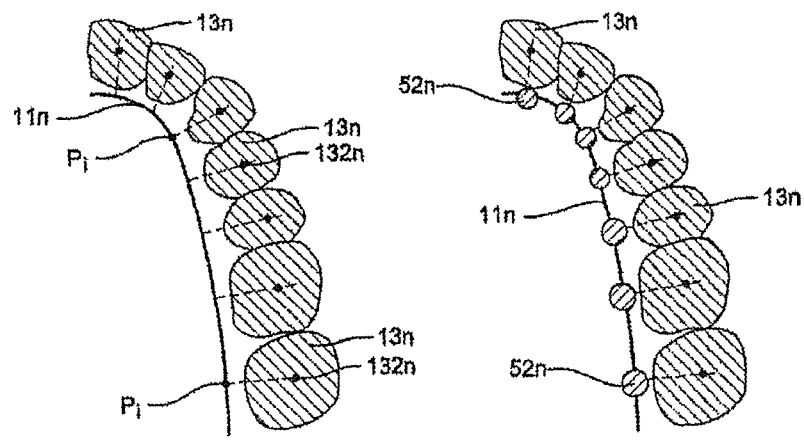
FIGS. 5a, 5b: an example of the various phases of the third step of the method, illustrating the numerical positioning of a second volume, representative of a bracket body of the bracket, on each tooth, for a cross section of a dental arch in a plane of the orthodontic archwire.

In a third step, as illustrated in FIGS. 5a and 5b, spheres 52n representative of the bracket bodies 122n are positioned individually with respect to each lingual surface 131n of the teeth 13n so that the orthodontic archwire 11n passes through them.

In one embodiment, as illustrated in FIG. 5a, in order to determine the position of a sphere 52n, a first phase is, for each tooth, to determine a centre 132n of the tooth 13n.

A second phase is to determine a position on the orthodontic archwire 11n of a point of reference of each sphere 52n. One way of determining the positions on the orthodontic archwire is, for example, to project the centre 132n of each tooth 13n orthogonally onto the orthodontic archwire 11n. The orthogonal projection of the centre of a tooth intersects the orthodontic archwire at a point $p_i$, the suffix i corresponding to the tooth, for example in accordance with the tooth numbering system laid down in the international standards (FIG. 5a).

In a third phase, the sphere 52n is positioned facing the relevant tooth so that a point of reference of the sphere corresponds to a point $p_i$ (FIG. 5b).

In one exemplary embodiment, the point of reference of a sphere 52n is its centre.

The operation of positioning the spheres 52n is repeated for all those teeth of the dental arch that require a bracket.

For preference, the spheres 52n have a dimension tailored to the dental anatomy. Thus, the spheres may, on the one hand, differ in size within one and the same dental arch for the same patient and, on the other hand, may differ in size for different patients.

For example, for one and the same patient with standard dentition, the spheres positioned on the lower incisors have a radius of the order of 2 mm and the spheres positioned on the teeth other than the incisors have a radius of the order of 2.5 mm.

Figure 6A:
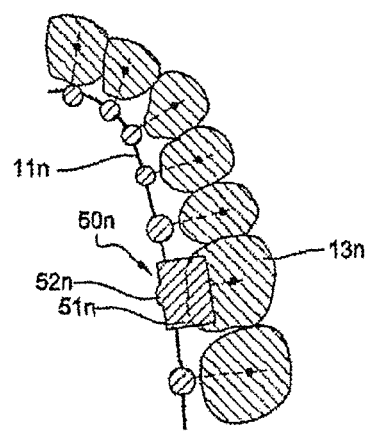
FIG. 6a: an illustration of the numerical positioning, on a tooth, of a blank with respect to the numerical representation of the orthodontic archwire and such that it interferes with the volume of the tooth, according to a fourth step of the method, for a cross section of a dental arch in a plane of the orthodontic archwire.
Figures 6B, 7:
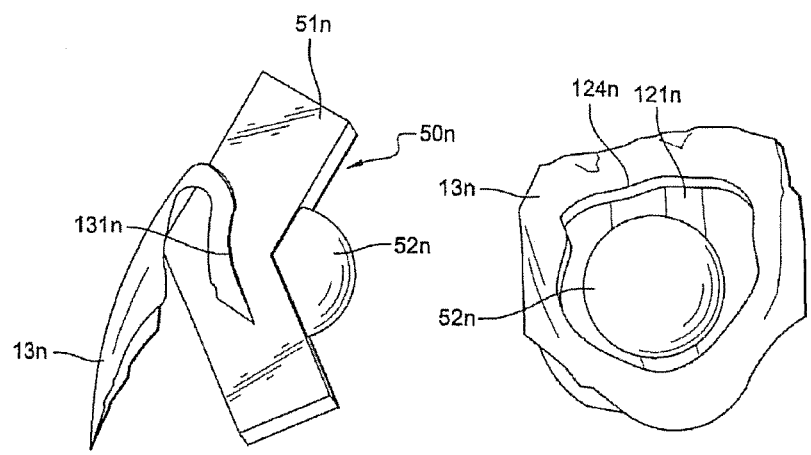
FIG. 6b: a perspective representation, for one tooth, of the numerical positioning of the blank such that it interferes with the volume of the tooth.
FIG. 7: an illustration of one form of bracket bonding pad obtained after the fifth step of the method.

In a fourth step of the method, as illustrated in FIGS. 6a and 6b, a blank 50n, formed on the basis of a first volume 51n associated with the sphere 52n, is positioned on each tooth 13n relative to the predefined orthodontic archwire 11n and such that it interferes with the volume of the tooth 13n.

For each blank 50n, the sphere 52n is positioned in accordance with the position determined beforehand in the previous step.

Each blank 50n is chosen and oriented in such a way that the first volume 51n is in tune with the anatomy of the relevant tooth, that is to say that the size, shape and orientation of the first volume 51n produces a finished area of intersection that is as great as possible with the lingual surface 131n of the tooth 13n considered.

Advantageously, the blank 50n is chosen from a collection of blanks of different shapes which may advantageously be available in a database comprising various numerical forms of the blanks 50n, the forms or shapes differing, for example, by having a concave shape or a convex shape, various sizes and various relative positions of the first volume 51n with respect to the sphere 52n.

For preference, the shape of the blank is chosen to suit the natural shape of the teeth and thus improve the later step of fabricating the bracket 12, by limiting the volume of material to be removed from the blank.

In one example of a shape, when the first numerical volumes 51n are preferably intended for the premolars and molars, the first volumes are concave bodies on the tooth side (FIG. 3a). When the first volumes are preferably intended for the canines and incisors, the second volumes are convex bodies on the tooth side (FIG. 3b).

In a fifth step of the method, as illustrated in FIG. 7, the volumetric exclusion zones of the first volume 51n of the blank 50n are determined and deleted, for each tooth 13n, so as to produce a numerical representation of a bracket bonding pad 121n.

In one embodiment of this fifth step, the volumetric exclusion zones are determined and deleted in three phases.

A first phase is to eliminate a volumetric exclusion zone of the first volume 51n which is common to the tooth 13n and to the blank 50n.

A second phase is to limit this volumetric exclusion zone to all or part of the lingual surface 131n of the tooth 13n so as to determine a perimeter of the bracket bonding pad 121n at a bearing surface 124n with the lingual surface 131n of the tooth 13n. The bearing surface thus defined conforms to the geometric shape of the lingual surface of the tooth. The bearing surface is defined by an area of intersection, delimited by a curve that is closed in space, between the first volume 51n and the lingual surface 131n of the tooth 13n. The area of intersection is defined in such a way that it covers as large an area as possible so as to obtain an interface that best meets the requirements for bonding, such as, for example, stability and retention, and occlusal comfort.

A third phase is to reduce a thickness of the remaining volume of the first volume. A numerical exclusion zone of the remaining volume of the first volume 51n is determined and deleted on a surface of the first volume 51n on the opposite side to the bearing surface 124n with the lingual surface 131n of the tooth 13n so as to limit the thickness of the bracket bonding pad 121n without, however, altering a zone where the first volume 51n meets the sphere 52n.

For preference, in order to reduce the dimensions of the final bracket for improved patient comfort, the bracket bonding pad 121n is produced in such a way that it has a substantially constant thickness which is thus as small as possible while at the same time being able to cope with the forces applied to the bracket.

This fifth step is implemented for each tooth 13n that requires a bracket.

At the end of this fifth step, each bracket 12n consists of the bracket bonding pad 121n firmly secured to the sphere 52n centred on the orthodontic archwire 11n. The bearing surface of the bracket bonding pad is defined in accordance with the geometric shape of the lingual surface of the teeth to make it possible, if necessary, for the final bracket to be repositioned accurately on the lingual surface during operation of rebonding the bracket.

Figures 8A, 8B:
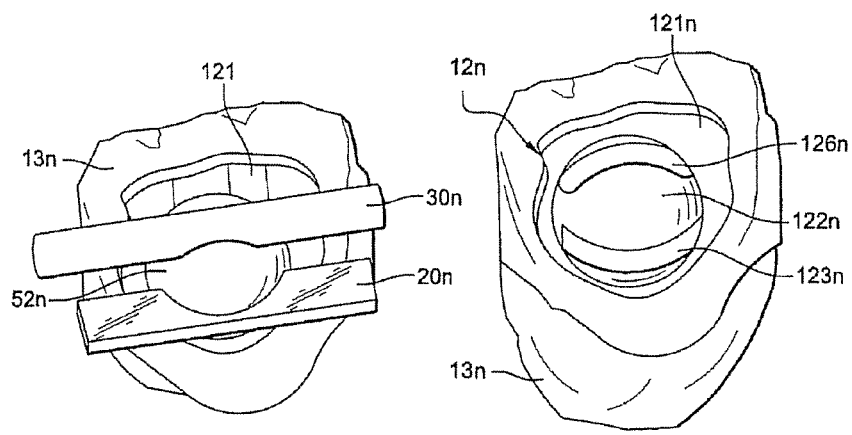
FIGS. 8a, 8b: an example of the various phases of the sixth step of the method, illustrating the production of a numerical representation of the bracket body from the determination and deletion of the volumetric exclusion zones in the second volume.

In a sixth step of the method, as illustrated in FIGS. 8a and 8b, volumetric exclusion zones of the sphere 52n are determined and deleted, for each tooth 13n, so as to produce a numerical representation 122n of a bracket body.

In one embodiment of this sixth step, the volumetric exclusion zones are determined and deleted in two phases.

In a first phase, an exclusion zone is determined to produce a housing 123n to accommodate the orthodontic archwire or orthodontic archwire self-ligating means.

In one embodiment of the first phase, the volumetric exclusion zone representative of the housing 123n is produced in the plane of the orthodontic archwire on a diameter of the sphere 52n in the direction of the orthodontic archwire and forms an open slot on one surface of the sphere 52n so as to design a slot 123n open in the direction of the concave side of the orthodontic archwire. The volumetric exclusion zone is produced in such a way that the slot has minimum height wise dimensions equal to or greater than the maximum thickness dimensions of the orthodontic archwire in the relevant sector of the dental arch.

One way of determining the volumetric exclusion zone is to design a zone of intersection between the sphere 52n and a first cylinder 20n, for example of substantially rectangular or square cross section, with its largest transverse dimension greater than the diameter of the sphere and its smallest dimension equal to or greater than the maximum thickness dimension of the orthodontic archwire, in the relevant sector of the dental arch.

In another embodiment of the second phase, the volumetric exclusion zone, of a size, in cross section, tailored to the cross-sectional dimensions of the orthodontic archwire, is no longer a slot but a hole. The volumetric exclusion zone is produced in such a way as to have cross-sectional dimensions substantially equal to the cross-sectional dimensions of the orthodontic archwire, in the relevant sector of the dental arch, and is produced in the plane of the orthodontic archwire 11n on a diameter of the sphere 52n. This embodiment is particularly well suited to the back molars.

One way of determining the volumetric exclusion zone representative of the hole is to design a zone of intersection between the sphere and the cylinder (not depicted) passing through the sphere, with its largest transverse dimension smaller than the diameter of the sphere.

Further, for preference, for certain brackets of the orthodontic appliance, particularly the brackets that have an open slot, at least one volumetric exclusion zone is determined to produce at least one secondary slot 126n to accommodate at least one ligature.

The at least one volumetric exclusion zone representative of at least one secondary slot is produced at the surface of the sphere and is positioned, for example, substantially parallel or perpendicular to the housing 123n.

One way of determining a volumetric exclusion zone is to design a zone of intersection between the sphere 52n and a second cylinder 30, for example of cylindrical cross section, said zone of intersection having the shape and the depth desired for the secondary slot 126n.

For preference, two zones of intersection are produced on the sphere in diametrically opposite positions.

In a second phase, all the volumetric exclusion zones of the sphere are deleted to form the at least one secondary slot 126n and the housing 123n to accommodate the orthodontic archwire.

In one particular embodiment of the method, the sixth step includes an additional phase of determining and deleting a volumetric exclusion zone so as to produce a slit to accommodate a fixing of a temporary ancillary accessory.

The volumetric exclusion zone is produced at the surface of the sphere, for example, positioned preferably at right angles to the slot 123n.

One means for determining the volumetric exclusion zone is to design a zone of intersection between the sphere 52n and a third tube (not depicted), for example of rectangular or square or circular cross section. The volumetric exclusion zone corresponding to the zone of intersection of the sphere and of the third tube is then deleted.

On completion of this sixth step, as illustrated in FIG. 8b, the numerical representation 12n of the bracket thus designed is a three-dimensional numerical object comprising a bracket bonding pad 121n and a bracket body 122n, produced to meet the customized requirements for each of the patient's teeth in the context of a protocol for reconfiguring a dental arch of the patient.

There is no set order in which to perform steps five and six and, according to the method, these steps may be carried out in the opposite order to the order described or may be carried out simultaneously without thereby changing the outcome of the steps.

For one particular embodiment, when the blank 50n comprises a third volume (not depicted) representative of a permanent ancillary accessory secured to the bracket, the method comprises an additional step of determining and of deleting volumetric exclusion zones of the third volume in order to design the final shape of the ancillary accessory.

This additional step may be carried out between the step of determining the exclusion zones of the first volume and the step of determining the exclusion zones of the second volume or after the step of determining the exclusion zones of the second volume.

The seventh step consists in physically producing the elements of the bracket 12 for the virtual representation 12n of the bracket designed previously.

In this seventh step of the method, a bracket 12, for each tooth 13, is fabricated from an actual blank 50, the blank being produced in a biocompatible material in accordance with the numerical blank selected during the fourth step of the design of the bracket 12, in the numerical process.

For example, the numerical object, representative of the final bracket, is exported in the form of numerical files to a machine tool or some other device intended to manufacture the final bracket from a biocompatible material using known methods.

In one exemplary embodiment of the seventh step, the bracket 12 is manufactured by machining. The numerical files are imported to a multi-axis machine tool in which the machining sequences are programmed. An actual blank 50 corresponding to the bracket 12 the numerical representation 50n of which was used is placed in the work zone of the machine and is then machined.

In another exemplary embodiment of this seventh step, manufacture is performed using a laser sintering technique or a grinding technique, using the exported numerical files. These techniques in particular can more easily produce the square-section or rectangular-section housings, slots, secondary slots in the bracket bonding pad or the bracket body of the bracket.

This seventh step is performed for each bracket of the orthodontic appliance.

The invention is described in the case of substantially spherical bracket bodies although this choice does not restrict the invention. Thus, other shapes of bracket body, for example rounded or blunted shapes, may also be used to improve patient comfort or display particular advantages for the production of the secondary slots. A person skilled in the art will be able to adapt this invention to suit bracket body shapes that have not been described.

The invention has been described in the preferred case of a flat orthodontic archwire, on the one hand because the forces applied by flat archwires are best suited to buccal physiology, and on the other hand because they can be produced on an industrial scale. The method according to the invention makes it possible to produce an orthodontic appliance which has no difficulty in responding to this choice of a flat archwire. However, this choice is not a limitation of the invention and a person skilled in the art will be able to adapt the invention to bended arches for orthodontic appliances intended for specific dentitions.

The brackets thus produced are tailored to form an orthodontic appliance for each patient and are customized to suit each of the patient's teeth.

Incorporated herein by this reference are various patents and patent publications that one of skill in the art will appreciate can be used in conjunction with the teaching and guidance provided herein to perform particular operations on various devices and in varying conditions. For the purposes of brevity while still complying with written description and enablement requirements, the following are hereby incorporated herein by this reference in their entireties: U.S. Pat. Nos. 7,811,087; 7,850,451 and 6,776,614.

In still other embodiments, an orthodontic bracket is disclosed herein for retaining one or more archwires in position. The bracket includes a base having a tooth affixing side and an opposing side, and there is one or more archwire retention channels extending in the mesial-distal directions. Each of the archwire retention channels includes a pair of inverted archwire retaining regions on one side of the channel, wherein each of the retaining regions, in turn, includes a recess that opens generally towards an opposing side of the channel, the opposing side being, in one embodiment, part of the bracket base. Each such recess is for grasping or holding an archwire within the channel having the recess. A first of the archwire retention channels includes a first pair of gingivally located inverted archwire retaining regions whose recesses hold a common archwire. In an embodiment of the bracket having more than one archwire retention channel, a second of the archwire retention channels includes a second pair of occlusally located inverted archwire retaining regions whose recesses hold another archwire. Moreover, for each of the archwire retention channel(s), there is a corresponding archwire retaining ridge extending gingivally-occlusally along the opposing side bracket base between the two archwire retaining regions of the channel, wherein this retaining ridge contacts a portion of an archwire that faces away from the archwire portion being held in the recesses of the inverted archwire retaining regions for the channel. Accordingly, for each pair of archwire retaining regions and an archwire held by the pair, the corresponding archwire retaining ridge exerts a force on the archwire directed toward the interiors of the recesses of the inverted retaining regions of the pair. In particular, this force assists in seating the archwire in the retaining regions of the pair.

Figure 10A:
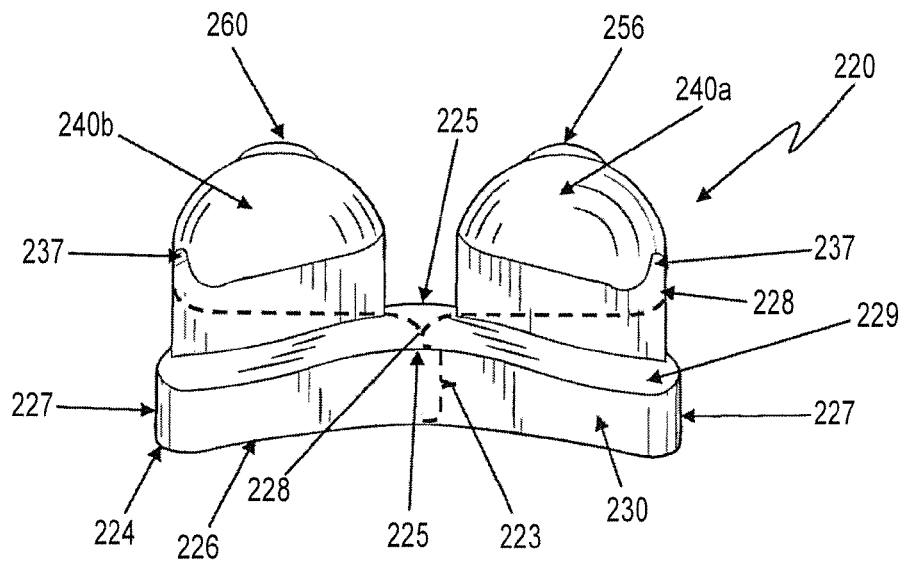
FIG. 10A is a gingival view of the bracket 220 of FIG. 9, wherein the retaining ridge 225 and the archwire retention channel 228 are shown.
Figure 10B:
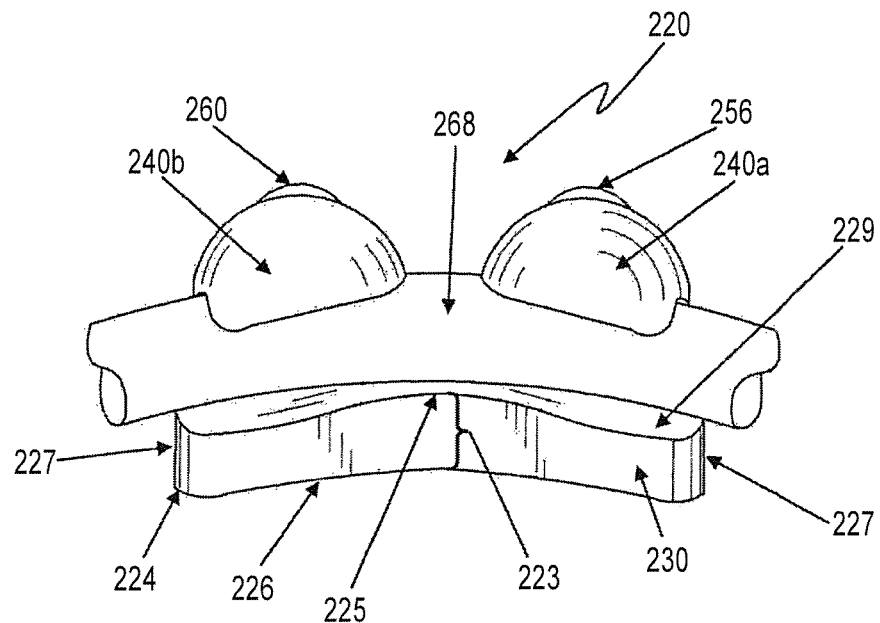
FIG. 10B is a gingival view of the bracket of FIG. 9 with an archwire 268 passing through archwire retention channel 228 (as shown in FIG. 10A), wherein the archwire is held in place in the retaining regions 240a, b by, e.g., the retaining ridge 225.

In particular for the at least one of the archwire retention channel included in the bracket and an archwire provided therein, the elasticity of the archwire to retain an initial non-curved shape causes the archwire to resist a channel induced bow in the archwire (such bowing or curving shown in FIG. 10B). Thus, as an orthodontist positions the archwire in the at least one channel of the bracket, the corresponding retaining regions for the channel together with the corresponding retaining ridge, bind or wedge the archwire within the channel. Accordingly, the opposing forces between the channel and archwire secure the archwire within the channel. Thus, it is a feature of the bracket 220 that for each such archwire channel, there are channel archwire bowing portions that retain the archwire within the channel, wherein a spaced apart plurality of these bowing portions (e.g., 240a and 240b for channel 228) contact the archwire at spaced apart locations on one side of the archwire's length, and wherein between such locations, there is at least one additional channel archwire bowing portion on an opposite side of archwire for inducing the archwire to press against the spaced apart plurality of contacting portions. Thus, the spaced apart plurality of bowing portions, and the at least one additional bowing portion induce oppositely directed forces on the archwire (such forces being traverse to the length of the archwire), and causing the archwire to bow or bend somewhat and to press against these bowing portions for holding the archwire within the channel. Said differently, the channel effectively is effectively bowed along its length.

In some embodiments, one archwire retention channel may be configured to provide more than a single bow or bind of the archwire within the channel. In particular, such a channel may be configured so that an archwire contained therein must form at least one "S" shape with the channel.

The novel bracket preferably has a generally square bracket base with opposing mesial-distal sidewalls, and opposing gingival-occlusal sidewalls that extend between the tooth affixing side and the opposing side (also referred to as an "upper side" herein). Each of the above described retaining ridges is provided by a corresponding thickened portion of the bracket base that extends in the gingival-occlusal direction of the bracket approximately along a gingival-occlusal center line of the bracket base. The thickened portion gradually thins in the mesial-distal direction of the bracket, ending with the same thickness as the gingival-occlusal sidewalls.

Two archwire retention bridges are also included on the novel bracket, wherein each end of each bridge includes one of the inverted archwire retaining regions from a different one of the first and second pairs identified above. A central archwire retention channel (positioned between the two archwire retention channels described above) extends in the mesial and distal direction along a central portion of the bracket. This channel is formed by the two archwire retention bridges which enclose spaced apart portions of the archwire retention channel for securing an archwire therein.

Embodiments of the bracket may be made of stainless steel for strength or other materials, including ceramics, plastics, polycrystalline alumina material, alumina (aluminum oxide), and zirconia. The bracket base design allows for the bracket to be used in both direct and indirect bonding to patients' teeth. Embodiments of the bracket may be formed via an injection molding technique.

Such a universal bracket design may be primarily attached to the lingual side of patients' teeth, but for embodiments of the bracket attached the labial/buccal side of a patients' teeth, the bracket base tooth facing curvature may be specific to particular tooth types.

Figure 9:
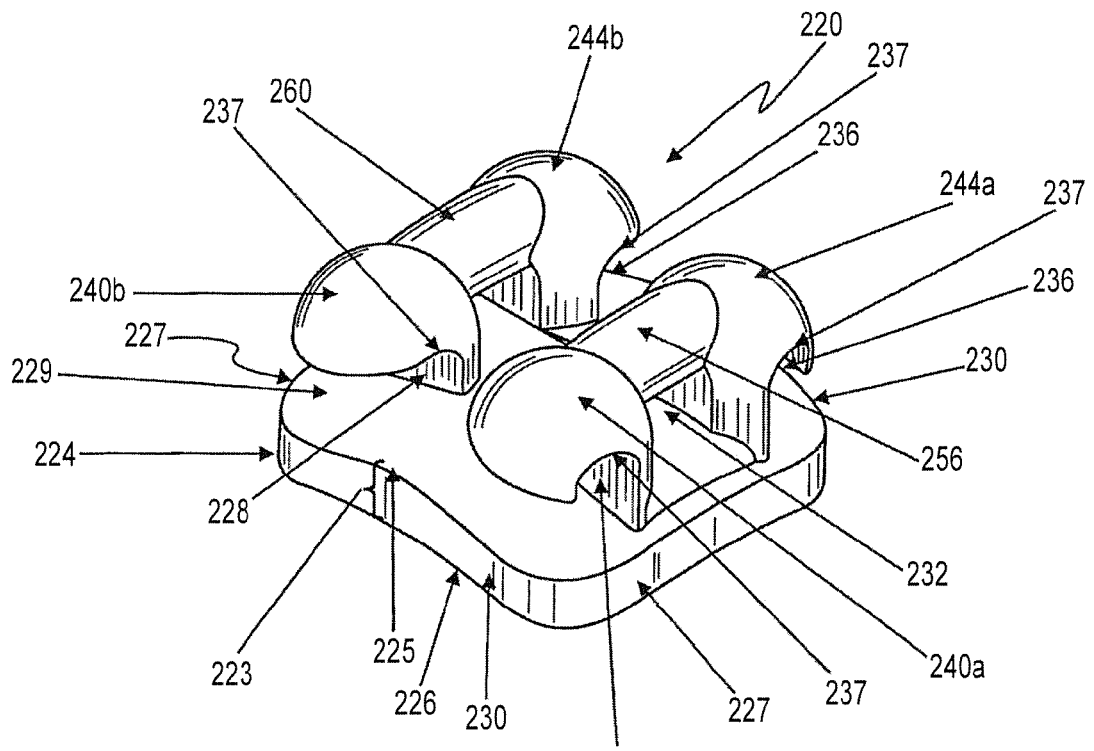
FIG. 9 is a perspective view of a bracket 220 illustrating novel features for an orthodontic bracket.
Figure 11A:
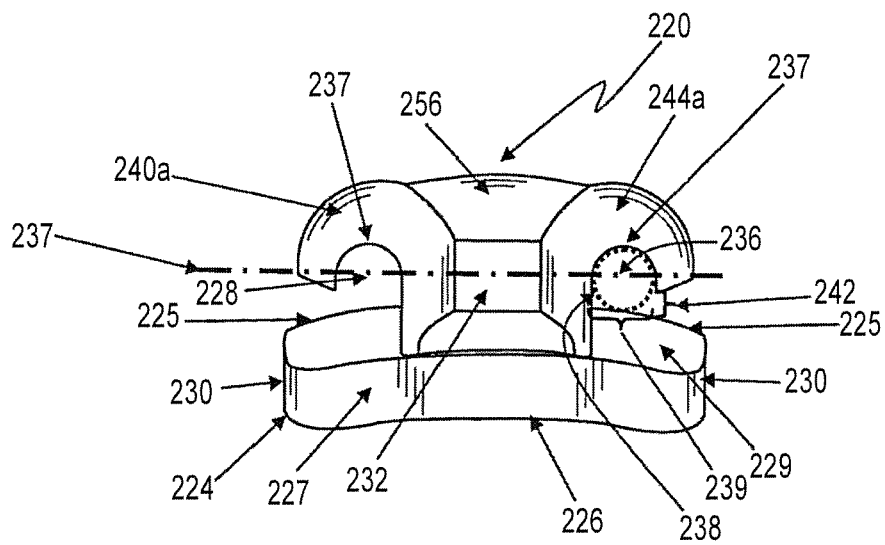
FIGS. 11A and 11B are side views of the bracket 220 of FIG. 9 looking through the archwire retention channels 228, 232 and 236.

Referring to FIGS. 9-16, various embodiments of a bracket 220 are shown, wherein the bracket includes:

(a) A generally square bracket base 224 having an upper side 229, a tooth affixing side 226, opposing mesial-distal sidewalls 227, and opposing gingival-occlusal sidewalls 30 as shown in FIGS. 9, 10A and 10. Additionally, the bracket base 224 has a pair of retaining ridges 225 extending from each of the opposing gingival-occlusal sidewalls 230 toward the interior of the upper side 229. FIGS. 9 and 10A show one of retaining ridges 225; FIG. 11A shows both retaining ridges. Each of the retaining ridges 225 is provided by a corresponding thickened portion 223 (FIGS. 9, 10A and 10B) of the bracket base 224 that extends in the gingival-occlusal direction of the bracket 220 approximately along a gingival-occlusal center line of the bracket base 224 (e.g., along the line L of FIG. 12). The thickened portion 223 gradually thins in the mesial-distal direction of the bracket 220, ending with the same thickness as the sidewalls 227.

(b) A pair of inverted archwire retaining regions 240a and 240b on the gingival side of the bracket 220 (FIGS. 9 and 10A), and another pair of inverted archwire retaining regions 244a and 244b (FIG. 9) on the occlusal side of the bracket. Each of the pairs (240a,b and 244a,b) is for retaining a respective archwire (e.g., archwire 268, FIG. 10B) therein. In particular, each of the inverted archwire retaining regions 240a and 240b provide a recess 237 (FIGS. 9 and 10A) for grasping or holding an archwire provided therein. Also, each of the inverted archwire retaining regions is attached to (and generally integral with) a corresponding support 239 (FIG. 10A) that connects the retaining region with the bracket base 224. Each support 239 extends outwardly from the upper side 229 by a distance somewhat larger than the cross section of largest archwire to be retained in the recesses 237. Moreover, each of the recesses 237 has an edge 243 (FIGS. 10A,B and 11B) that is spaced apart from the support 239 for the recess, wherein the distance between the edge and the support is also somewhat larger than the cross section of largest archwire to be retained in the recesses 237.

Note that for each of the pairs of the inverted archwire retaining regions 240a,b and 244a,b, a corresponding one of the retaining ridges 225 (FIGS. 9, 10A, 10B and 11A) assists in securing an archwire (e.g., archwire 268) in the two recesses 237 of the pair. Accordingly, for each of the pairs 240a,b and 244a,b, the recesses 237 for the pair operatively cooperate with a corresponding one of the retaining ridges 225 to provide a corresponding archwire retention channel, i.e., for an archwire retention channel 228, the pair 240a,b, defines one side of the channel 228 (i.e., an "outer" side) and the corresponding retaining ridge 225 provides the opposing side of the channel 228 (i.e., an "inner" side), and for an archwire retention channel 236, the pair 244a,b, defines one side of the channel 236 (i.e., an "outer" side) and the corresponding retaining ridge 225 provides the opposing side of the channel 236 (i.e., an "inner" side). Thus, when an archwire is received (and held) in the inverted archwire retaining regions 240a,b or 244a,b (i.e., archwire retention channel 228 or 236), this archwire is operatively coupled together with the bracket attached to a patient's tooth.

(c) Two archwire retention bridges 256 and 260 (FIGS. 9, 10A, 10B, 12, 13, 14 and 15), wherein each end of each bridge attaches to one of the inverted archwire retaining regions and/or the support 239 therefor. For example, i.e., the ends of the bridge 256 may be attached to the inverted archwire retaining regions 240a and 244a (or attached to the support 239 therefor), and the ends of the bridge 260 may be attached to the inverted archwire retaining regions 240b and 244b (or attached to the support 239 therefor).

(d) An archwire retention channel 232 (FIGS. 9, 11A, and 13) extending in the mesial and distal direction along a central portion of the bracket 220. The two archwire retention bridges 256 and 260 (together with their corresponding inverted archwire retaining regions) enclose, and substantially define, spaced apart portions of the archwire retention channel 232 for securing an archwire therein (FIG. 16B).

The bracket base 224 may be made of a variety of materials, but in one embodiment may be stainless steel for strength. However, other materials may be used including ceramics and plastics. The remainder of the bracket 220 may be composed of various materials in addition to those recited above (e.g., polycrystalline alumina material, alumina (aluminum oxide), zirconia). In one embodiment, the bracket 220 may be formed via an injection molding technique.

The bracket base 224 may be a universal bracket design in that it can be attached to the surface of various tooth types (e.g., incisor, bicuspid, molar, etc). Moreover, such a universal bracket design does not require bracket identification to aid in identifying placement of the bracket and/or identifying a particular embodiment of the bracket 220. Such a universal bracket design also leads to simplified inventory management since only one embodiment of the bracket 220 may be needed for placement on all teeth types instead of different embodiments of the bracket for different teeth types. However, such universal bracket design may be primarily for the lingual side of patients' teeth. For embodiments of the bracket 220 to be provided on the labial/buccal side of patients' teeth, the curvature of the tooth affixing side 226 may be specific to particular tooth types as one skilled in the art will understand. Accordingly, it is also within the scope of the present disclosure that markings or identifications may be provided on embodiments of the bracket 220 for identifying the bracket (e.g., as a universal bracket, or specific to a particular tooth type(s)), for identifying the manufacturer or distributor of the bracket, and/or for identifying a particular placement or orientation of the bracket on a tooth or tooth type. Note that descriptions of providing such markings and/or identifications are disclosed in U.S. Patent Application Publication 2008/0020338 filed Jul. 24, 2007 and published Jan. 24, 2008, this application being fully incorporated herein by reference.

The bracket base 224 design allows for the bracket 220 to be used in both direct and indirect bonding. Note that the term direct bonding refers to applying adhesive directly to a patient's tooth and subsequently attaching a bracket 220 thereto. Indirect bonding refers to positioning one or more brackets 220 on a dental cast of a patient's teeth. The dental cast, having the brackets 220 attached thereto, is then surrounded with a material, wherein the material, once solidified, secures the brackets therein and can act as a transportation device for the brackets once the dental cast is dissolved away. Adhesive is then applied to the back of each of the brackets 220 prior to placing the transportation device containing the brackets onto the patient's teeth. Accordingly, in the indirect bonding technique, all of the brackets 220 are bonded to the patient's teeth simultaneously. Once the brackets 220 are bonded, the transportation device is removed from the teeth, leaving behind the brackets attached to the teeth.

Regarding the retaining ridges 225 described above, each such ridge corresponds to a maximal offset from the tooth affixing side 226 along a corresponding one of the archwire retention channels 228 and 236. Moreover, in at least some embodiments, such a ridge 225 has its maximal offset centered on line L of FIG. 12. In the embodiment of the bracket 220 shown in FIGS. 10A and 10B, the contour of each of the retaining ridges 225 is a smooth arc without undulations in the mesial-distal direction, and may also be a smooth arc in the gingival-occlusal direction without undulations. However, it is within the scope of the present disclosure that in the gingival-occlusal direction, such a ridge 225 may reach its maximal offset at any point where the ridge transverses its corresponding archwire retention channel (228 or 236) as long as the ridge effectively assists in wedging or holding an archwire in the channel (i.e., the recesses 237 of the channel). Thus, the thickened portion 223 (FIG. 9) for each retaining ridge 225 may induce a force upon an archwire 268 or 264 (e.g., FIG. 13) to retain it in the archwire retaining regions of the corresponding archwire retention channel 228 or 236. Note that each of the two retaining ridges 225 may have symmetrical profiles (i.e., mirror images of one another about the center line L of FIG. 12, and about mesial-distal center line through the bracket). Moreover, note that the maximal offset for a retaining ridge 225 may occur just outside its corresponding archwire retention channel, e.g., on the mesial-distal perimeter of the channel furthest from the central retention channel 232. Such placements of the maximal offsets may not only provide forces for securing an archwire within the corresponding recesses 237, but also apply a force on the archwire for inhibiting the archwire from moving in a direction generally lateral to the upper side 229.

In another embodiment of the bracket 220, the retaining ridges 225 may have a larger or smaller maximal offset from the tooth affixing side 26 to the upper side 229 of the bracket base 224 when compared to the embodiments of the figures. Moreover, one of the retaining ridges 225 may have a larger maximal offset from the tooth affixing side 226 than the other retaining ridge 225. This variance in the maximal offset of the retaining ridges 225 may allow for and aid in the retention of different diameter archwires in the retaining regions 240a,b and 244a,b.

In another embodiment of the bracket 220, one or more of the retaining ridges 225 may have a corresponding secondary retaining ridge located at the gingival or occlusal edges of the bracket base 224. These secondary retaining ridges may be located on the upper side 229 at the gingival and/or occlusal edges of the bracket base 224. Such secondary retaining ridges may extend in the mesial-distal direction on the upper side 229 of the bracket base 224. The secondary retaining ridges may have varying shapes (e.g., hemispherical or elliptical). Accordingly, the retaining regions 240a,b and 244a,b, in conjunction with the secondary retaining ridges, keep the corresponding archwire secured in one of the corresponding archwire retention channels 228 and 236 (more specifically their recesses 227).

For further description of the archwire retention channels 228, 232 and 236, reference is made to FIG. 11A which provides a lateral (side) view of the bracket 220 along a gingival-occlusal side. The center archwire retention channel 232 of the bracket 220 is enclosed by the two spaced apart portions of the archwire retention bridges 256 and 260 (FIGS. 9, 10A, 10B, 12, 13, 14 and 15), and the upper side 229 of the bracket base 224. As described above, each of the gingival archwire retention channel 228 and the occlusal archwire retention channel 236 is provided by: (i) partially enclosed spaced apart recesses 227 of a pair of inverted archwire retaining regions, respectively, 240a,b or 244a,b, and (ii) the upper side 229 of the bracket base 224. Both the gingival archwire retention channel 228 and the occlusal archwire retention channel 236 may be mirror images of one another. Each of the inverted archwire retaining regions 240a,b for the gingival archwire retention channel 228, and each of the retaining regions 244a,b for the occlusal archwire retention channel 236 may be generally circular in profile (as shown in, e.g., FIG. 11A). Each such profile may generally match the curvature of, e.g., the cross section of a corresponding archwire to be provided therein. In FIG. 11A, a dashed circular cross section 238 of such an archwire is shown in the archwire retaining regions 244a,b of the occlusal archwire retention channel 236. The diameter 239 of the archwire retention channel 236 may be sufficiently surrounded by the inverted archwire retaining regions 244a,b to grip and retain the archwire therein. In at least one embodiment, the opening 242 for receiving the archwire into the channel 236 is preferably approximately the same size as the diameter of the archwire cross section 238 along the axis 237, e.g., smaller or larger by approximately 0.01 to 0.02 inches. As also illustrated in FIG. 11A, each of the inverted archwire retaining regions 244a, b may surround somewhat more than 180 degrees of the circular cross section of an archwire positioned in the occlusal archwire retention channel 236. Note that a similar description can also be provided for the gingival archwire retention channel 228 in that the channel 228 may be a mirror image of occlusal archwire retention channel 236. However, it is within the scope of the present disclosure that the gingival archwire retention channel 228 may be configured differently from the occlusal archwire retention channel 236, e.g., the gingival archwire retention channel 228 may secure different sizes of archwires therein from the archwires for the occlusal archwire retention channel 236. Also, either or both of the archwire retention channels 228 and 236 may have an elliptical profile or other profile instead of the circular profile shown in FIG. 11A. Further, an embodiment of the bracket 220 may have only one of the archwire retention channels 228 or 236.

Figure 11B:
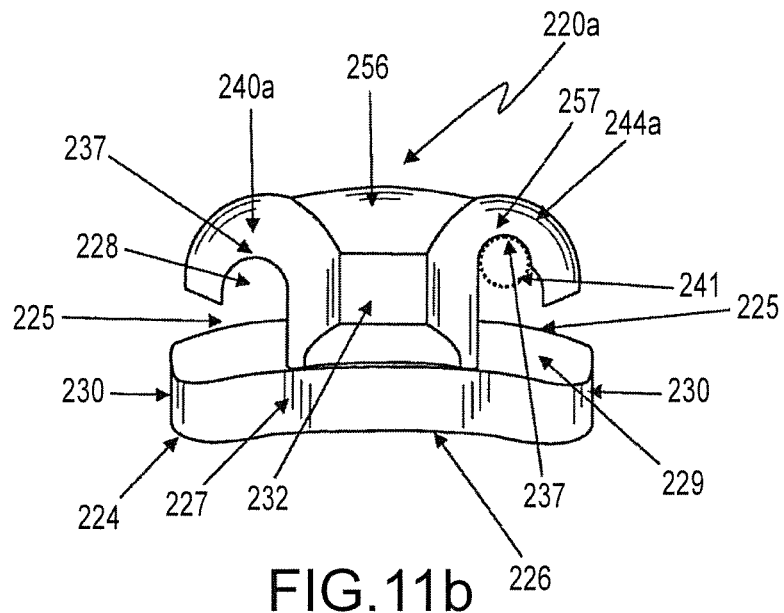

Referring to FIG. 11B, an embodiment of the bracket 220A is shown that includes a retaining region (e.g., 244a) that is shaped or configured to retain archwires having substantially different cross sectional diameters. An archwire having a diameter 239 (FIG. 11A) may be snapped into the retaining region 244a as indicated in FIG. 11A. However, an archwire having a much smaller cross section 241, as shown in FIG. 11B, may also be provided in the channel 236. In particular, the smaller diameter archwire may snap into (or is otherwise retained) in an upper section 257 of the retaining region. Note that in one embodiment, a bead (not shown) may be strung on this smaller diameter archwire such that the bead is positioned between the retaining regions 244a and 244b so that the bead contacts the corresponding retaining ridge 225 for the occlusal archwire retention channel 236 in a manner that assists in locking the archwire into the upper section 257.

Whether the bracket embodiment of FIG. 11A or 11B is provided, multiple sizes of archwires may be utilized in each of the archwire retention channels 228, 232 and 236. The range in the maximal cross sectional extent of the archwires that may be utilized can be from 0.008 inches to 0.024 inches, and such cross sections may be generally circular in cross sectional shape but different cross sectional shapes may be used, e.g., at least rectangular or square cross sectional shapes for the central archwire retention channel 232. The multiple sizes of archwires may provide varying forces and friction levels ranging from an alignment force having a low friction, to a leveling force having a moderate friction, to a finishing force having a maximum friction as one skilled in the art will understand. In particular, the inverted archwire retaining regions 240a,b and 244a,b allow for the archwires 268 or 264 (FIGS. 13, 14 and 15) to be attached to the bracket 220 without the use of ligatures.

In another embodiment, the archwire retaining regions 240a and 244a (or 240b and 244b) may be joined together, above the upper side 229. Such joining of the retaining regions for one of the archwire retention channels 228 or 226 may form a single integral retaining region, or the joining may be in form of a bridge there between similar to the bridges 256 and 260 (except extending in the mesial-distal direction rather than the gingival-occlusal direction). Regardless, there may be a cutout (not shown) over the corresponding retaining ridge 225 so that when the archwire contacts the retaining ridge 225, the archwire is wedged into this cutout. In another embodiment, there may be only one of the outer archwire retention channels 228 and 236 utilized to retain an archwire.

Figure 12:
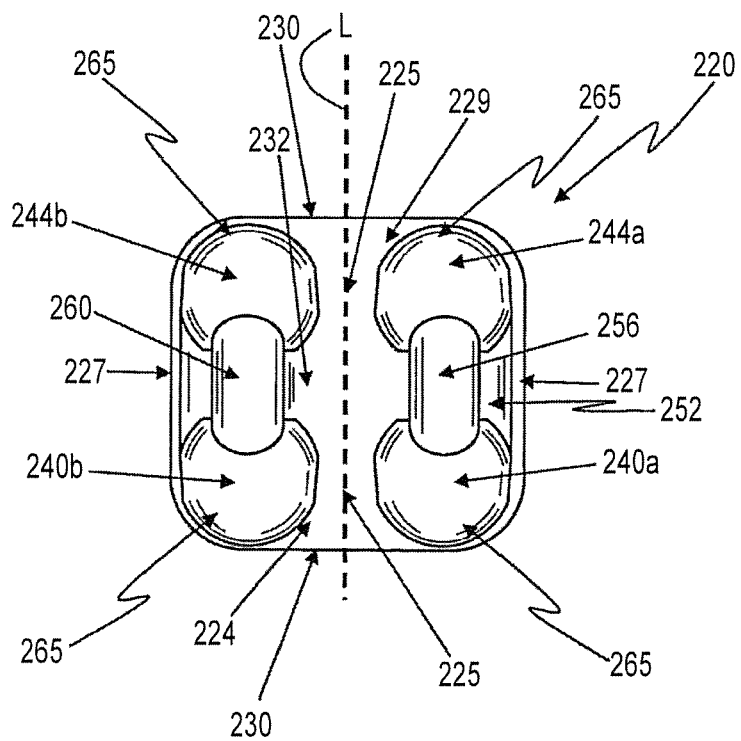
FIG. 12 is a top view of the bracket 220 of FIG. 9.

Referring to FIG. 12, a top view of the bracket 220 is shown wherein the center archwire retention channel 232 on the bracket is defined by the spaced apart portions of the archwire retention bridges 256 and 260 and the upper side 229 of the bracket base 224. The archwire retention bridges 256 and 260 connect and reinforce the inverted archwire retaining regions 240a to 244a and 240b to 244b. The smooth rounded contours and edges 265 of the inverted archwire retaining regions 240a, b and 244a, b provide for patient comfort, particularly when such brackets are placed on the lingual side of a patient's teeth. In the center archwire retention channel 232, the archwire is enclosed on all sides (FIGS. 11A and 11B) at two points along the channel, i.e., using the archwire retention bridges 256 and 260 (FIG. 12).

Figure 13:
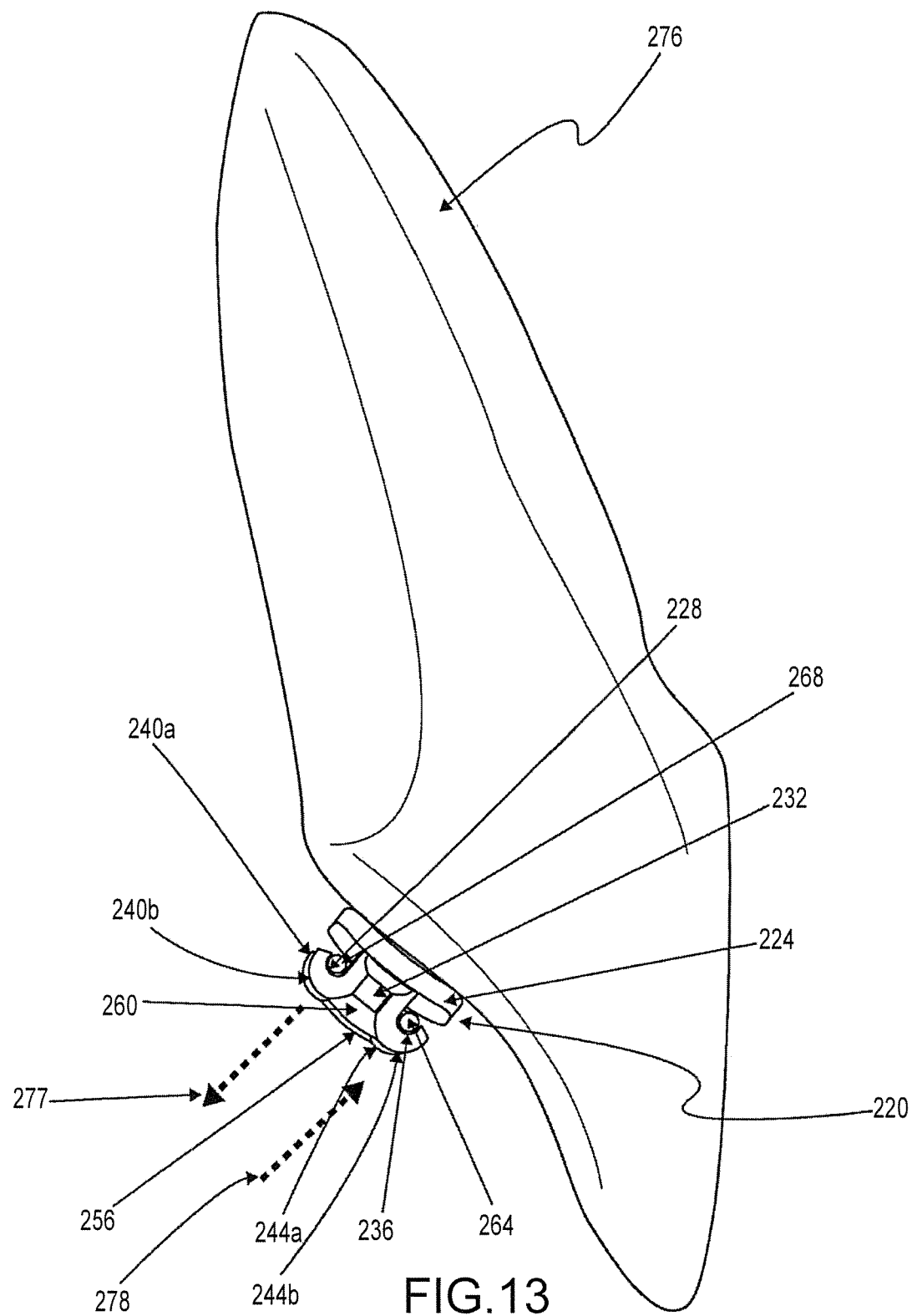
FIG. 13 is lateral perspective view of the bracket 220 of FIG. 9 with archwires 268 and 264 located in the gingival 228 and occlusal 236 archwire retention channels to provide, e.g., torque to a tooth 276 to which the bracket may be attached.

A lateral view of the bracket 220, as shown in FIG. 13, shows an archwire 264 in the occlusal archwire retention channel 236 and an archwire 268 in the gingival archwire retention channel 228. The occlusal 264 and gingival 268 archwires are held place via the friction system created by the inverted archwire retaining regions 240a,b and 244a,b in combination with the ridges 225 (not shown in FIG. 13). FIG. 13 also shows where the bracket 220 may reside on a tooth when it is bonded thereto. The arrows 277 and 278 (FIG. 13) indicate the forces for a torque that the bonded bracket 220 may apply to the tooth.

Figure 14:
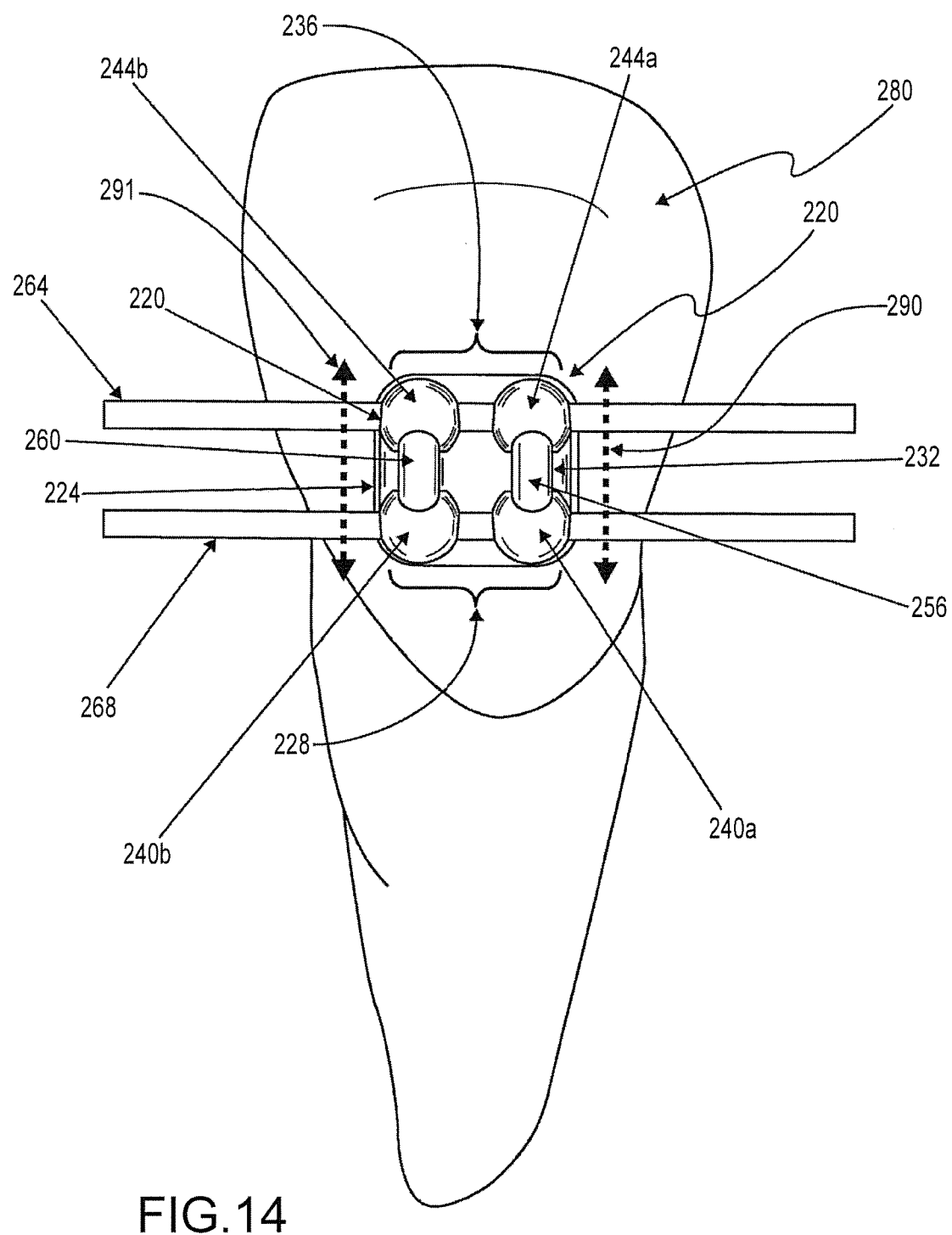
FIG. 14 is a top view of the bracket 220 of FIG. 9 with archwires 268 and 264 located in the gingival 228 and occlusal 236 archwire retention channels to provide tip to the tooth 280 to which the bracket is attached as one skilled in the art will understand.

FIG. 14 provides a top view of the bracket 220 bonded to a tooth 280 wherein there is an archwire 264 in the occlusal archwire retention channel 236, and an archwire 268 in the gingival archwire retention channel 228. The arrows 290 and 291 indicate the motion of tip (angulation) that the bracket 220 may apply to the tooth once it is bonded and the archwires are configured appropriately.

Figure 15:
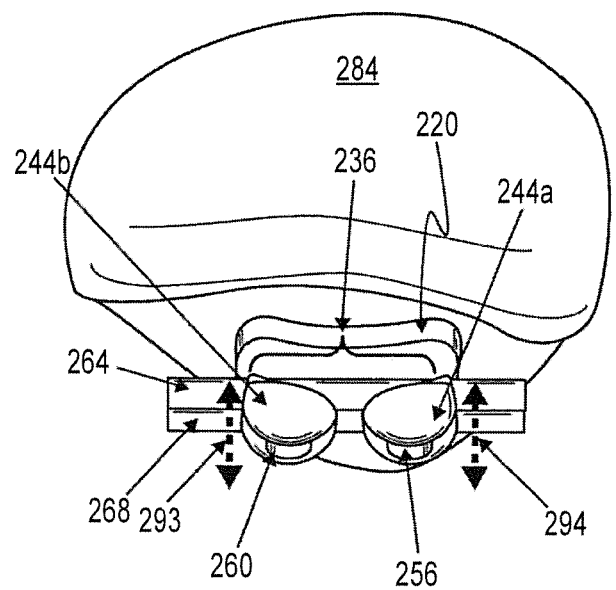
FIG. 15 is an end perspective view of the bracket 220 of FIG. 9 with archwires 268 and 264 located in the gingival 228 (not shown) and occlusal 236 archwire retention channels to provide rotation to the tooth 284 to which the bracket is attached as one skilled in the art will understand.

An end perspective view of the bracket 220 is shown in FIG. 15 with an archwire 264 in the occlusal archwire retention channel 236 and an archwire 268 in the gingival archwire retention channel 228. This figure also shows the bracket bonded to a tooth 284 thereby showing where the bracket 220 may reside on the tooth when it is bonded thereto. The arrows 293 and 294 indicate the motion of rotation that the bracket 220 and the archwires 264 and 268 may apply to the tooth.

Figure 16A:
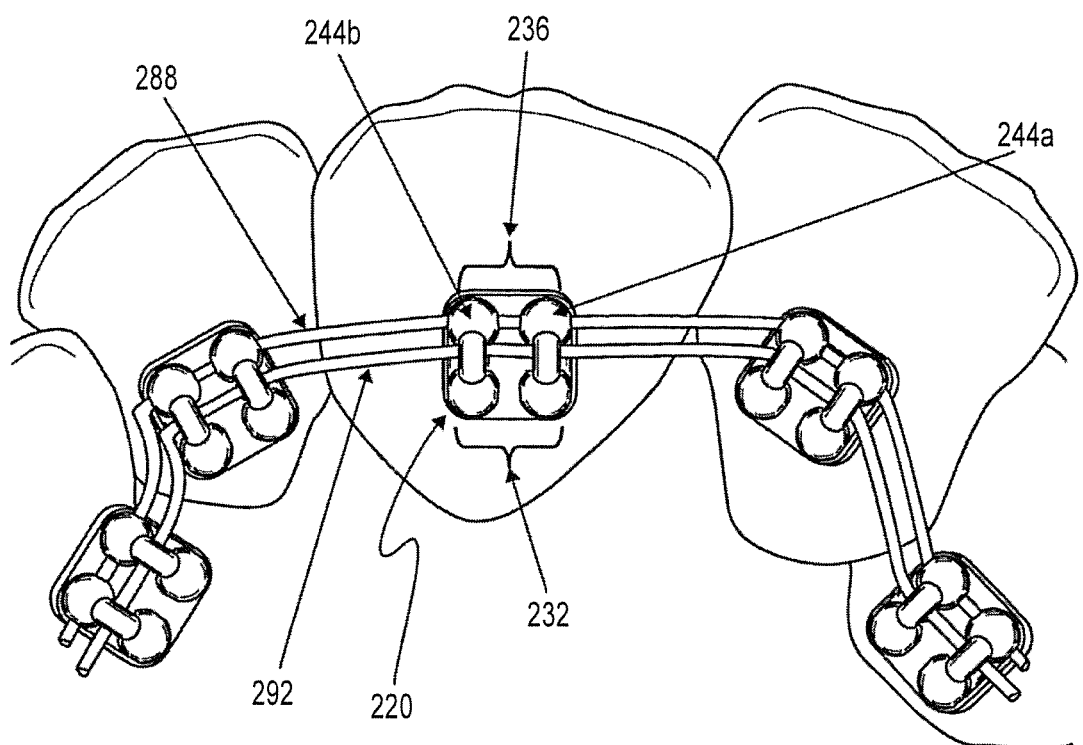
FIGS. 16A and 16B show an embodiment of the novel bracket 220 with different archwire configurations attached thereto.
Figure 16B:
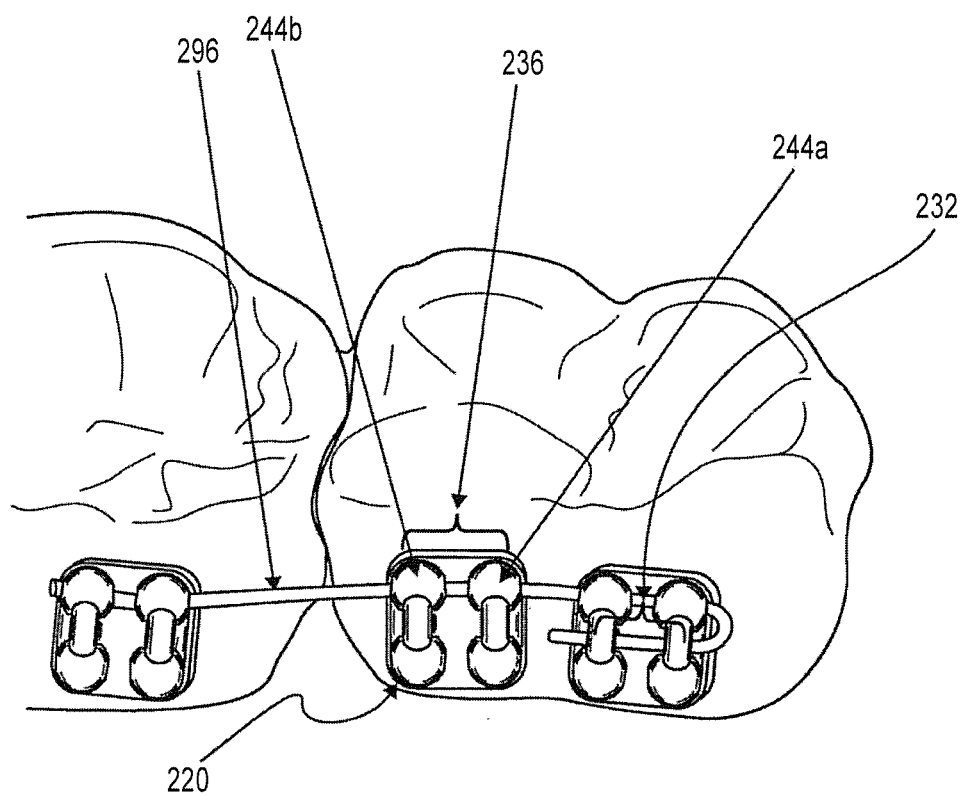

A plurality of the brackets 220 is shown connected together by archwires in FIGS. 16A and 16B. FIG. 16A shows the plurality of brackets 220 connected together by an archwire 288 extending through the corresponding occlusal archwire retention channels 236 of the brackets. FIG. 16A also shows a second archwire 292 secured in the center archwire retention channel 232 of the brackets 220, providing dynamic sectional control in the movement of the teeth, as one skilled in the art will understand. FIG. 16B displays how another configuration, wherein there is an archwire 296 in the occlusal archwire retention channel 236 of the brackets 220. The archwire 296 is also configured so that its end is secured in the center archwire retention channel 232 of the rightmost one of the brackets 220, thereby creating a loop like shape. It is worth noting that due to the diminutive size of the brackets 20 relative to the teeth to which they are attached (as shown in FIGS. 16A and 16B), the size of these brackets 220 may allow for the bonding of two such brackets 220 on a single tooth. For example, FIG. 16B shows two such brackets 220 affixed to a molar.

Alternative embodiments of the bracket 220 include providing the inverted archwire retaining portions so that instead of their recesses 237 opening toward the base 224, such recesses open in another direction (e.g., away from the base, or generally parallel with the upper side 229 of the base). In such embodiments, the retaining ridge 225 is also repositioned to face in the direction toward such recesses for retaining an archwire in the same manner as, e.g., shown in FIG. 10B except that the base 224 in this figure would no longer be the base of the bracket. Instead, the base would attach, e.g., to the top of the retaining portions 240a,b and 244a,b, or alternatively attach the bracket components shown FIG. 10B to a (new) bracket base that is oriented substantially perpendicular to the base shown in FIG. 10B.

In each of the embodiments of the bracket 220 disclosed hereinabove, at least one of the archwire retention channels 228 and 236 is provided, wherein for an archwire provided therein, the elasticity of the archwire to retain an initial non-curved shape causes the archwire to resist the channel induced bow in the archwire (such curving shown in FIG. 10B). Thus, as an orthodontist positions the archwire in the at least one channel of the bracket 220, the corresponding retaining regions (240 and 244) for the channel together with the corresponding retaining ridge 225 bind or wedge the archwire within the at least one channel. Accordingly, the opposing forces between the channel and archwire are believed to secure the archwire within the channel. Thus, it is a feature of the bracket 220 that for each such archwire channel (e.g., 228 and/or 236), there are channel archwire bowing portions that retain the archwire within the channel, wherein a spaced apart plurality of these bowing portions (e.g., 240a and 240b for channel 228) contact the archwire at spaced apart locations on one side of the archwire's length, and wherein between such locations, there is at least one additional channel archwire bowing portion on an opposite side of archwire for inducing the archwire to press against the spaced apart plurality of contacting portions. Thus, the spaced apart plurality of bowing portions, and the at least one additional bowing portion induce oppositely directed forces on the archwire (such forces being traverse to the length of the archwire), and causing the archwire to bow or bend somewhat and to press against these bowing portions for holding the archwire within the channel.

In use, after an orthodontist has secured the bracket 220 to one of a patient's teeth, the orthodontist may exert a force (e.g., substantially parallel to the upper side 229) on a corresponding archwire to force the archwire enter one or both of the archwire retention channels (228 or 236), wherein such force induces the corresponding archwire to bow in the channel. Alternatively, the orthodontist may thread the archwire into such a channel, wherein the orthodontist pushes the archwire into the channel by purposely bowing or binding the archwire to follow the bow of the channel, and then once the archwire is threaded through the channel, the orthodontist can then bend the archwire into the correct orientation to attach the archwire to, e.g., a next orthodontic appliance attached to, e.g., a next tooth. Note, that such subsequent bending of the archwire by the orthodontist is believed to also provide similar forces on the archwire (and traverse to the length thereof) as described above for securing the archwire within the channel.

Figure 17:
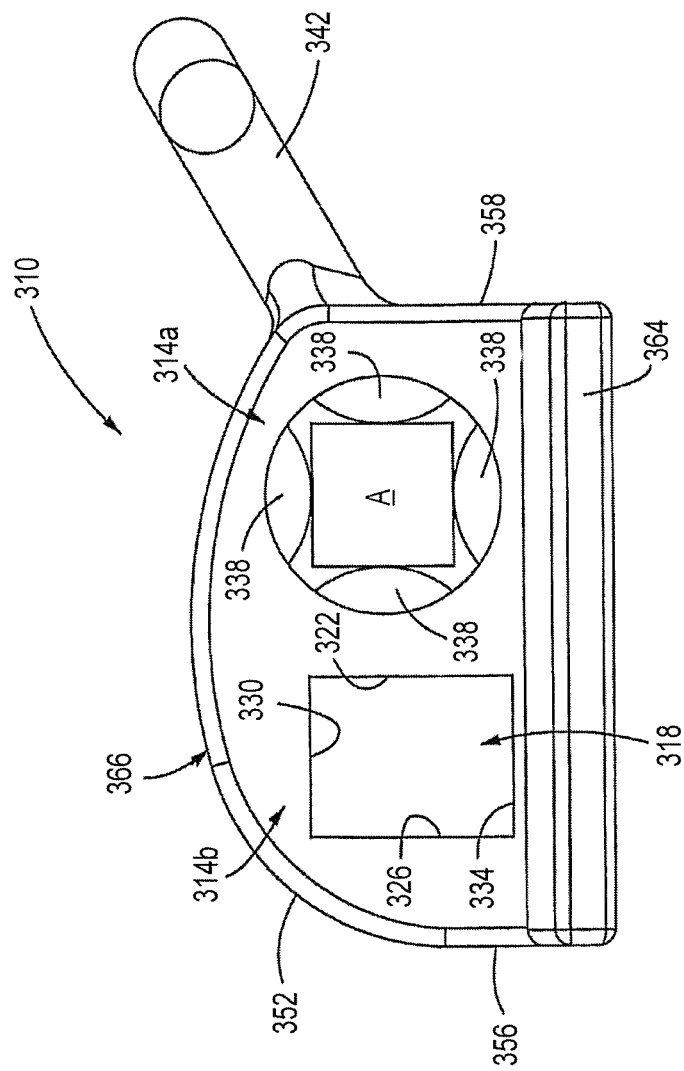
FIG. 17 is a side elevation view of a distal end of an orthodontic appliance in accordance with embodiments of the present invention.
Figure 20B:
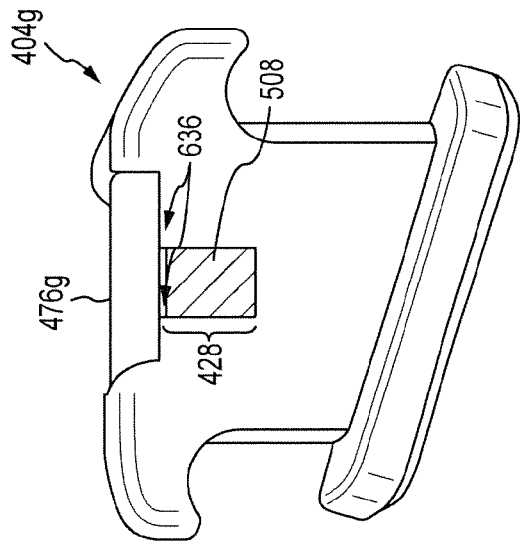
FIGS. 20A and 20B show views of the self-ligating orthodontic bracket 404g, wherein this bracket is in the actively closed configuration such that insertion and/or extraction of an archwire 504 from the bracket slot 428 is prevented by rotatable member 456g, and the archwire 504 is relatively firmly secured to the slot 428 to thereby prevent (or substantially inhibit) archwire movement therein. In particular.
Figure 20A:
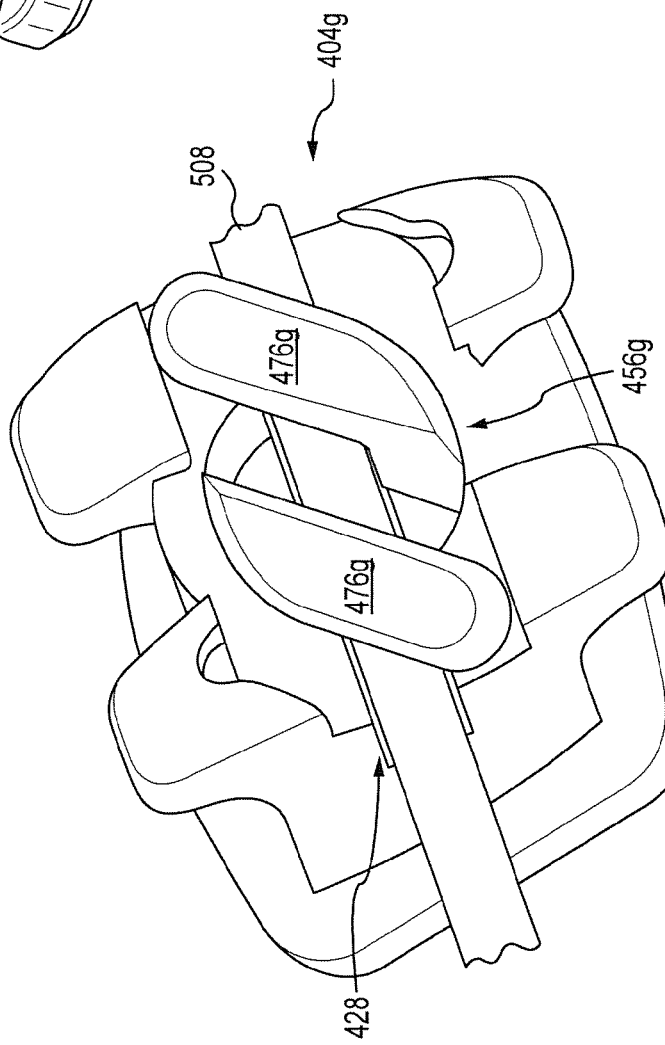

Referring now to FIG. 17, and in accordance with at least one embodiment of one or more inventions described herein, a tube 10 is shown having a pair of archwire/appliance slots/tubes 314a and 314b. The first archwire/appliance slot/tube 314a is substantially circular in cross section and includes a plurality of projections 338. The projections limit the surface area contact between the exterior sides of the archwire A and the interior of the archwire/appliance slot/tube 314a.

In a separate aspect of one or more embodiments of the one or more inventions described herein, a tube 310 is provided that has at least one archwire/appliance slot/tube that includes projections for reducing frictional interaction with an archwire, and at least one archwire/appliance slot/tube that does not include projections, such as for reducing frictional interaction with an archwire. Referring again to FIG. 17, the first archwire/appliance slot/tube 314a includes at least one projection 338, and a second archwire/appliance slot/tube 314b is depicted that does not include a projection 338.

In accordance with embodiments of the present invention, a method of adjusting the position of a tooth is provide, the method including attaching a tube to a tooth and inserting an archwire through an archwire slot in the tube. The method further includes limiting surface contact of the archwire along a portion of the longitudinal length of the archwire slot by contacting an exterior surface of the archwire with friction reducing features located within the archwire slot. More particularly, the method includes contacting the exterior surface of the archwire with one or more of the interior sides of the archwire slot, wherein the interior sides include a gingival side, an occlusal side, a side, and a lingual side. The friction reducing features preferably comprises at least one of: (a) a plurality of projections residing along a longitudinal length of one or more of the gingival side, occlusal side, side, and lingual side; and (b) a longitudinally extending projection residing along a longitudinal length of one or more of the gingival side, occlusal side, side, and lingual side. In accordance with embodiments of the present invention, one or more projections are located along a plurality of the gingival side, side, and lingual side of the interior of the archwire slot.

It should be understood that the scope of the present invention includes the use of a plurality of passageways, including at least one passageway, and more preferably, at least two passageways, and potentially three or more passageways in any particular device. Such passageways can be configured in various symmetrical shapes and configurations to include squares, rectangles, triangles, polygons, octagons, flat and curved sided configurations, etc. In a preferred embodiment, the geometrical configuration of a passageway mirrors the general exterior shape of an archwire used with such appliance. It is also within the scope of the present invention that frangible covers abutting or extending over an archwire placed within the orthodontic device of the present invention, be removable and/or adjusted in ways desired by an orthodontist. Thus, for example, materials rounding receptacle 68 can be constructed so as to be frangible and thus removable at some point in time after desired placement of a device and/or for orientation thereof. The number of receptacles 68 can include, for example, at least one receptacle suitable for manipulation by an orthodontist, but may also include one or more, two or more, or three or more such receptacles, which can, in certain embodiments, be adapted to correlate with the prongs of a receptacle engaging device or insertion tool. One of skill in the art will also appreciate the scope of the present invention includes the use of different geometrically configured passageways, such that a square archwire can be used in one passageway, whereas a round archwire can be used in an adjacent passageway, etc., with the passageways having a similar exterior configuration as the archwire utilized in such applications. Alternatively, the passageway or archwire slot may have a different geometric shape than that of the archwire used.

In one embodiment, lingual brackets of the present invention include an archwire tube comprising a buccal side, a lingual side, an occlusal side and a gingival side, wherein the buccal side comprises a friction reducing feature and wherein at least one of the group consisting of the gingival side, the occlusal side and the lingual side comprises a friction reducing feature. Preferably, a first of the friction reducing features comprises a projection extending substantially the length of said passageway and extending into said passageway. A second of the friction reducing features preferably comprises a plurality of separate projections residing along the length of the passageway and are spaced apart from each other along the length of said passageway.

In summation, a tube is provided that includes a number of novel features, including a friction reducing profile within the tube opening, modified exterior shaping to facilitate improved comfort, and a plurality of positioning notches, recesses, gripping portions or placement notches for receiving an installation tool. For the above-described tube 310, placement of the archwire/appliance slot/tube 314 on a band can cover any angle, mesial/distal locations, gingival/occlusal or lingual locations, and any direct bond applications.

Texturing of the lingual surface of orthodontic brackets has been used to provide improved bonding between the bracket and the tooth to which the bracket is applied. For example, U.S. Pat. No. 5,522,725, incorporated herein by reference, concerns a method of improving the bond strength of a plastic bracket by temporarily heating and then permanently deforming projections located on the base of the bracket. The deformed projections interlock with adhesive when the bracket is bonded to a tooth. U.S. Pat. No. 5,595,484, incorporated herein by reference, discloses a plastic bracket having a metal reinforcement member partly embedded in the bracket body. FIG. 13 of the '484 patent discloses a bracket base having eight recessed discontinuous portions 36 that include molded identification characters 35. U.S. Pat. No. 5,622,494 (the '494 Patent), incorporated herein by reference, discloses several structures, including a spiral-like ridge, concentric rectangles, and a weave pattern. Upon being deformed, each structure creates an undercut structure for forming a mechanical bond with an adhesive. A base structure may also that include lettering, symbols, or numerals that are substantially continuous and that functionally serve as texturing to enhance the adhesive bonding surface of, e.g., an orthodontic appliance to a patient's tooth.

As illustrated in FIGS. 18A-21, for example, in one or more embodiments of the present invention, slot coverable extensions can be configured so that in at least one rotatable position such extensions cause or induce an archwire in the slot to be "actively" held in place within the slot, wherein, for example, the extensions (or another bracket component) contacts the archwire for causing or forcing the archwire into contact with the surfaces of the slot (e.g., a floor of the slot) with sufficient force to induce frictional forces there between such that (for orthodontic purposes) such frictional forces effectively inhibit movement of the archwire in a direction along the length of the slot. Additionally/alternatively, the slot coverable extensions can be configured so that in at least one rotatable position such extensions cause or induce an archwire in the slot to be "passively" held in place within the slot, wherein, for example, the extensions (or another bracket component) only loosely restrains the archwire to remain in the slot in a manner such that the archwire can readily move in a direction along the length of the slot. In particular, in the passive archwire restraining configuration, there is insufficient frictional forces between the archwire and the slot (for orthodontic purposes) to effectively inhibit movement of the archwire in a direction along the length of the slot. Moreover, in one or more embodiments of the bracket, the slot coverable extensions can be rotated from a passive configuration to an active configuration, and/or from an active configuration to a passive configuration.

In still other embodiments, the self-ligating orthodontic bracket includes a bracket body with an archwire slot, at least two, but in other embodiments four or more, spaced apart mounting arms having mounting slots, and a mounting pin permanently or removably mounted in the mounting slots. A closure member may be mounted to the body of the bracket and movable between a reversibly closed position in which at least a portion of the archwire slot is covered and an open position, in which the archwire slot is uncovered. The closure member may have various elements that slide, rotate, pivot, and/or enclose that can be mounted to the body of the bracket.

Yet another embodiment provides a self-ligating orthodontic bracket that includes a mounting base for attachment to a tooth surface, an archwire slot formed upon the base and sized for receiving an orthodontic archwire, a rotary ligating cover selectively rotatable between an open position permitting access to the archwire slot and a closed position covering the archwire slot, and one or more locking features for holding the rotary cover in a closed position. Such locking feature may be positioned and designed to cooperatively mate with other designated portions of the bracket so as to achieve desired reversible engagement and open-retention features may also be provided that facilitate the purposeful opening of the locking feature to permit manipulation of the bracket, archwire, etc. as deemed appropriate by either the orthodontist or the patient.

Other embodiments are directed towards an orthodontic self-ligating bracket provided with a cover that can be rotated over an arch wire slot in the base portion to close when a frangible portion is severed upon initiating rotation of the cover. Such cover rotates about a hinge, which may include a pin or axle that can be moved laterally and/or vertically after the frangible portion is severed and preferably is manufactured to form one piece, such as using an injection molding, machining, or casting process, thus avoiding additional subsequent assembly to attach a cover to a base.

Some embodiments employ a self-ligating orthodontic bracket clip slidably engagable with the bracket to allow the clip to slidably move between an open position and a closed position in which the clip extends across the archwire slot to retain the archwire in the archwire slot.

Other embodiments employ a replaceable closing spring member detachably connected to a base member to maintain pivoting engagement of such spring member when desired and easy removal of the spring members when desired.

Other self ligating bracket designs include a latching member having a hinge pin made of a flexible material so that a portion of the latching member is engagable with the bracket.

In some embodiments, a range of adjustability is provided in the range of motion of a closing or locking member, thus limiting the forces encountered by an archwire held in the archwire slot, thus permitted desired sliding of the archwire in the slot. To accomplish this end, a camming mechanism can be employed. The bracket body may be formed from a non-metallic material, such as a polymer, a filled polymer composite, or a ceramic, and the self-ligating mechanism may be formed from a metal. A resilient engagement member with a detent positioned to engage an aperture can be employed to achieve secure closure.

To further an appreciation of the various designs of the present disclosure and to assist in providing requisite support of written description and enablement of the various features of the present disclosure, the following references are hereby incorporated herein by reference in their entries: 20110081622 to Mashouf; U.S. Pat. No. 7,695,277 to Stevens; 20100203463 to Huff; U.S. Pat. No. 7,780,443 to Hagelganz; 20110076633 to Bryant; 20100285421 to Heiser; 20100159411 to Oda; 20100062387 to Hilliard.

FIGS. 18-21 show embodiments of a bracket 404g having a rotatable member 456g which, in turn, includes slot coverable extensions 476g that are substantially straight and bar shaped. FIGS. 18A and 18B show the rotatable member 456g in the open position wherein the archwire 504 is not secured in the slot 428 by the extensions 476g. Tie wings 432L and 432R of the bracket may be of various sizes and shapes, or may be eliminated in certain embodiments. Alternatively, FIGS. 19A and 19B show the rotatable member 456g in a first closed position, wherein the archwire 504 is passively restrained to the slot 504. Additionally, FIGS. 20A and 20B show the rotatable member 456g in a second closed position, wherein the archwire 504 is actively restrained to reside in the slot 428.

In FIG. 21, all three bracket 404g configurations: open, passively closed, and actively closed are shown from left to right, wherein the difference these configurations is primarily the rotation of the rotatable member 456g relative to the bracket body 408g. In particular, relative to the (left most) open bracket configuration in FIG. 21, the passively closed (middle) bracket configuration has the rotatable member 456g rotated through an angle 644, and the actively closed (right most) bracket configuration has the rotatable member rotated through an angle 648. Note that the angle 644 may be in a range of 20° to 45°, and the angle 648 may be in a range of 30° to 90°.

Figure 22A:
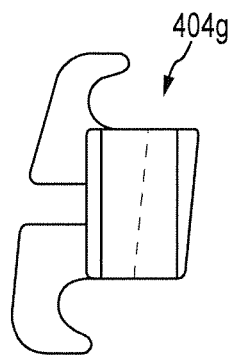
FIG. 22A shows a side view of a bracket and a bracket bonding pad of the bracket.
Figure 22B:
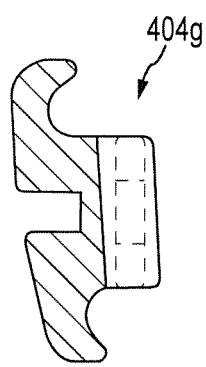
FIG. 22B shows another side view of different embodiment of a bracket and a bracket bonding pad of the bracket.

FIG. 22a-FIG. 22b illustrate side views of brackets and bonding pads that may be employed in various embodiments of the present invention. In particular, for a lingual bracket system, preferably at least one slot, more preferably two, and in still other embodiments more than two slots, either horizontal slots and/or vertical slots, but more preferably horizontal slots, are employed on a plurality of the brackets used. Brackets may be designed for different teeth configurations, such as those depicted in FIGS. 22a-b. In FIG. 22a for example, the wings are straight out (see lower left of figure) and is thus designed to lie substantially flat on the lingual surface of the tooth. In FIG. 22b, however, the wings are deflected upward. Thus, as one of skill in the art will appreciate, when used in a lingual bracket system, several brackets having wings with various deflections may be used to fit the contour of different lingual teeth. Therefore, the present invention in some embodiments provides for the ability to avoid having to manufacture custom brackets for each patient, and instead, several designs of stock brackets may be provided so that any given patient's teeth configuration can be addressed via standard brackets that can be mass produced. Computer aided implementation and selection of appropriate brackets to form a complete lingual bracket system is thus facilitated.

The disclosure herein has been describes preferred embodiments of the invention claimed hereinbelow; however, other changes and modifications to the claimed invention may be made which are still contemplated within the spirit and scope of the present disclosure.

The foregoing disclosure has been provided for purposes of illustration and description. This disclosure is not intended to limit the invention claimed hereinbelow, and various embodiments thereof. Variations, embodiments and modifications will be apparent to those skilled in the art and are intended to be within the scope of the following claims.

What is claimed is:

1. A method of producing a customized orthodontic appliance comprising:
   scanning a model of a dental arch using computer software to generate a 3D numerical representation of a dental arch;
   constructing, by a processing device, a numerical representation of a bracket for said dental arch, the operation of constructing comprising:
   positioning a numerical representation of an orthodontic archwire with respect to a dental arch final numerical representation, then for each relevant tooth of the dental arch final numerical representation, positioning a second volume of a bracket blank, comprising a numerical representation of a volume representative of an envelope volume of a bracket body, such that the second volume of a bracket blank interferes with the numerical representation of the orthodontic archwire and in close proximity to the relevant tooth, and for each relevant tooth of the dental arch final numerical representation, positioning a first volume of the bracket blank such that the first volume interferes with the second volume and with the volume of the relevant tooth, then determining, for each relevant tooth in the first volume and in the second volume, volumetric exclusion zones, said volumetric exclusion zones containing all of the volumes that interfere with the relevant tooth for the first volume and all of the volumes that interfere with the orthodontic archwire for the second volume, wherein the numerical representation of the bracket of one relevant tooth is determined by the volume of the bracket blank minus said volumetric exclusion zones, and the blank is chosen from a database comprising at least two models of a numerical representation blank;
   and wherein the numerical representation blank is chosen in relation to the shape of the relevant tooth so as to minimize the volume of the exclusion zones while at the same time keeping an aerial contact between a bearing surface of the bracket bonding pad and the surface of the relevant tooth.

2. The method according to claim 1, wherein the numerical representation of the orthodontic archwire is positioned in such a way that a distance, for each tooth of the dental arch final numerical representation, between the numerical representation of the orthodontic archwire and the surface of each tooth is greater than a minimum distance d.sub.min that corresponds to a minimum thickness of the numerical representation of the bracket at its bracket body.

3. The method according to claim 1, wherein, for each tooth of the dental arch final numerical representation, the numerical representation of the second volume is positioned in such a way that a reference point of the second volume corresponds to a point of intersection between the numerical representation of the orthodontic archwire and an orthogonal projection of a center of the relevant tooth.

4. The method according to claim 1, wherein housings are produced, for at least one sector of the dental arch, with a cross section appreciably larger than a cross section of the orthodontic archwire so that the orthodontic archwire can slide naturally along the dental arch in the housings as the teeth of the dental arch move.

5. The method according to claim 1, wherein the orthodontic appliance is produced from a flat orthodontic archwire.

6. The method according to claim 1, wherein the numerical representation of the brackets is placed on lingual surfaces of the teeth of the dental arch final numerical representation.

7. The method according to claim 6, wherein the bracket is produced from a biocompatible material in accordance with the numerical representations.

8. The method according to claim 1, wherein the numerical representation of the brackets is placed on vestibular surfaces of the teeth of the dental arch final numerical representation.

9. The method according to claim 1, wherein the exclusion zones of the second volume determine a housing in the form of an open slot in the numerical representation of the bracket body to accommodate the numerical representation of the orthodontic archwire.

10. The method according to claim 1, wherein the exclusion zones of the second volume determine a housing in the form of a tube in the numerical representation of the bracket body to accommodate the numerical representation of the orthodontic archwire.

11. The method according to claim 1, wherein the volumetric exclusion zones are determined in a numerical representation of at least one volume representative of an envelope volume of an ancillary accessory, known as a third volume, of the bracket blank, and are then subtracted from the blank.

12. The method according to claim 1, wherein the final numerical representation of the dental arch desired at the end of the treatment of the patient is produced from a numerical representation of the dental arch of the patient prior to treatment.

13. A method of producing a customized orthodontic appliance comprising:
    scanning a model of a dental arch using computer software to generate a 3D numerical representation of a dental arch;
    constructing, by a processing device, a numerical representation of a bracket for said dental arch, the operation of constructing comprising:
    positioning a numerical representation of an orthodontic archwire with respect to a dental arch final numerical representation, then for each relevant tooth of the dental arch final numerical representation, positioning a second volume of a bracket blank, comprising a numerical representation of a volume representative of an envelope volume of a bracket body, such that the second volume of a bracket blank interferes with the numerical representation of the orthodontic archwire and in close proximity to the relevant tooth, and for each relevant tooth of the dental arch final numerical representation, positioning a first volume of the bracket blank such that the first volume interferes with the second volume and with the volume of the relevant tooth, then determining, for each relevant tooth in the first volume and in the second volume, volumetric exclusion zones, said volumetric exclusion zones containing all of the volumes that interfere with the relevant tooth for the first volume and all of the volumes that interfere with the orthodontic archwire for the second volume, wherein the numerical representation of the bracket of one relevant tooth is determined by the volume of the bracket blank minus said volumetric exclusion zones, and the blank is chosen from a database comprising at least two models of a numerical representation blank;
    wherein the numerical representation blank is chosen in relation to the shape of the relevant tooth so as to minimize the volume of the exclusion zones while at the same time keeping an aerial contact between a bearing surface of the bracket bonding pad and the surface of the relevant tooth; and wherein the orthodontic appliance is produced from a flat orthodontic archwire and the numerical representation of the brackets is placed on lingual surfaces of the teeth of the dental arch final numerical representation.

14. The method according to claim 13, wherein the numerical representation of the orthodontic archwire is positioned in such a way that a distance, for each tooth of the dental arch final numerical representation, between the numerical representation of the orthodontic archwire and the surface of each tooth is greater than a minimum distance d.sub.min that corresponds to a minimum thickness of the numerical representation of the bracket at its bracket body.

15. The method according to claim 13, wherein, for each tooth of the dental arch final numerical representation, the numerical representation of the second volume is positioned in such a way that a reference point of the second volume corresponds to a point of intersection between the numerical representation of the orthodontic archwire and an orthogonal projection of a center of the relevant tooth.

16. The method according to claim 13, wherein housings are produced, for at least one sector of the dental arch, with a cross section appreciably larger than a cross section of the orthodontic archwire so that the orthodontic archwire can slide naturally along the dental arch in the housings as the teeth of the dental arch move.

17. The method according to claim 13 wherein the numerical representation of the brackets is placed on vestibular surfaces of the teeth of the dental arch final numerical representation.

18. The method according to claim 13, wherein the exclusion zones of the second volume determine a housing in the form of an open slot in the numerical representation of the bracket body and wherein the bracket is produced from a biocompatible material.

19. The method according to claim 13, wherein a bracket produced from the final numerical representation of the dental arch is positioned on the lingual side of a patient's teeth.

* * * * *